United States Patent
Kasuga et al.

(10) Patent No.: US 6,372,943 B1
(45) Date of Patent: Apr. 16, 2002

(54) POLYENEPOLYCARBOXYLIC ACIDS, DERIVATIVES THEREOF WITH RESPECT TO CARBOXYL GROUPS, OR SALTS OF THESE

(75) Inventors: Shinobu Kasuga, Suita; Toshihito Kakiuchi, Tsuchiura; Ryo Yamanishi, Nishinomiya; Kazuki Okada, Ichinomiya, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/623,475

(22) PCT Filed: Mar. 11, 1999

(86) PCT No.: PCT/JP99/01170

§ 371 Date: Oct. 30, 2000

§ 102(e) Date: Oct. 30, 2000

(87) PCT Pub. No.: WO99/46231

PCT Pub. Date: Sep. 16, 1999

(30) Foreign Application Priority Data

Mar. 13, 1998 (JP) ............................................ 10-063754

(51) Int. Cl.$^7$ ........................ C07C 57/02; C07D 307/60
(52) U.S. Cl. ........................ 562/595; 560/190; 549/233; 549/252
(58) Field of Search ........................ 509/595; 560/190; 549/233, 252

(56) References Cited

PUBLICATIONS

David C. Aldridge, et al., J.C.S. Perkin I, pp. 2134–2135, "A New Tricarboxylic Acid Anhydride from Paecilomyces Variotii", 1980.

A. Jabbar, et al., Pharmazie, vol. 50, pp. 706–707, "Isolation and in Vitro Antibacterial Screening of a Tricarboxylic Acid Anhydride from Penicillium Sp.", 1995.

Bruce C. Gilbert, et al., Journal of the Chemical Society, Perkin Transactions 2, No. 2, pp. 1345–1356, "Electron Spin Resonance Evidence for Rapid Cyclization of Alkenyl Radicals Formed by Readily Occurring 1,5–and 1,6–Hydrogen Shifts in Vinyl Radicals", 1986.

James Foxall, et al., Journal of the Chemical Society, Perkin Transactions 2, No. 2, pp. 273–278, "Radical Addition to Alkynes: Electron Spin Resonance Studies of the Formation and Reactions of Vinyl Radicals", 1980.

*Primary Examiner*—Paul J. Killos
(74) *Attorney, Agent, or Firm*—Oblon, Spivak, McClelland, Maier & Neustadt, P.C.

(57) ABSTRACT

Polyenepolycarboxylic acids represented by the following formula (1);

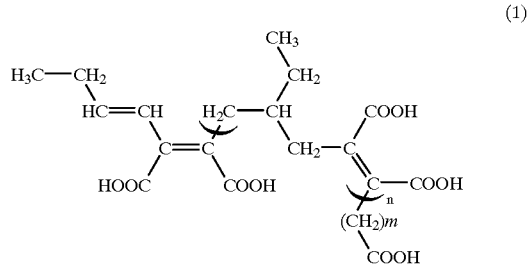

(1)

(wherein n represents an integer of 0 to 5 and m represents an integer of 1 or 2, provided m is 1 when n is 0), or derivatives thereof at their carboxyl group(s) or their salts.

The above compounds originate from natural products and are capable of exhibiting excellent dispersing ability.

25 Claims, No Drawings

POLYENEPOLYCARBOXYLIC ACIDS, DERIVATIVES THEREOF WITH RESPECT TO CARBOXYL GROUPS, OR SALTS OF THESE

TECHNICAL FIELD

The present invention relates to novel polyenepolycarboxylic acids, or derivatives thereof at their carboxyl group (s) or their salts (which may hereinafter be referred to as "polyenepolycarboxylic acids" simply), anr d more specifically, to such polyenepolyearboxylic acids having superior dispersing ability which are produced by microorganisms belonging to genus Talaromyces.

BACKGROUND ART

Heretofore, there have been used surface active agents, macromolecular polymers and the like as dispersants for industrial purposes in a variety of fields such as pigments, coatings, cosmetic articles, coated paper, dyes, ceramics, and building and civil engineering, and particularly in recent years such compounds have been generally used in the production of fine particles.

Since these compounds thus widely used as dispersants for industrial purposes are frequently synthetic organic compounds, such compounds mostly are inferior in safety, biodegradability and like characteristics though possessing excellent dispersing ability. Therefore, depending on the manner of use, there is a fear that such compounds may raise problems such as bad influence on living bodies, environmental pollution, and scattering of such compounds in the environment.

Attention is now focused on dispersants originating from natural products which exhibit superiority in both the biodegradability and safety and hence are friendly to the terrestrial environment. Examples of such dispersants include xanthan gum, which is a polysaccharide produced by a microorganism and which is widely used in various industrial fields, taking advantage of its viscosity. However, xanthan gum has poor dispersing ability with respect to inorganic or oleaginous ingredients used in pigments, coatings and the like though offering superior safety.

Other such dispersants include saccharic acids such as sodium gluconate, which are used in a part of industry but find a limited range of application as dispersants since situations and sorts of dispersoids to which they are applicable are limited.

Accordingly, it has been earnestly desired to provide a compound originating from a natural product which is capable of exhibiting superior dispersing ability irrespective of the sort of dispersoid be used.

DISCLOSURE OF INVENTION

A compound according to the present invention having attained the above object is characterized by polyenepolycarboxylic acids represented by the following formula (1):

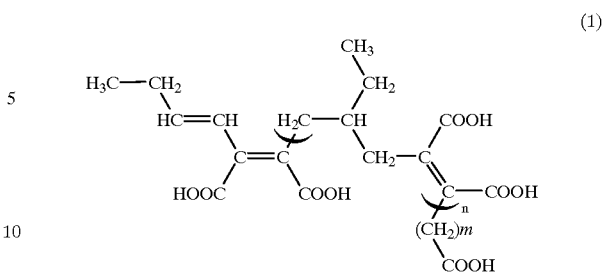

(wherein n represents an integer of 0 to 5 and m represents an integer of 1 or 2, provided m is 1 when n is 0), or derivatives thereof at their carboxyl group(s) or their salts. Those compounds of the above formula (1) wherein m=1 and n=0; m=2 and n=1; m=2 and n=2 are preferred embodiments of the present invention.

A dispersant according to the present invention having attained the above object is characterized by containing polyenepolycarboxylic acid(s) represented by the above formula (1) wherein n represents an integer of 0 to 5, and m represents an integer of 1 or 2, or derivatives thereof at their carboxyl group(s), or their salts. Any of those compounds of the above formula (1) wherein m=2 and n=0; m 2 and n=1; m=2 and n=2 is a preferred embodiment of the present invention.

The polyenepolycarboxylic acids represented by the above formula (1) (wherein n represents an integer of 0 to 5 and m represents an integer of 1 or 2), or acid antydrides thereof or their s alts are prepared by the use of a culture solution obtained by cultivating a microorganism belonging to genus Talaromyces in a culture medium dand hence, such a preparation method is included in the scope of the invention. Also, the microorganisms that produce the polyenepolycarboxylic acids represented by the above formula (1) (wherein n rep resents an integer of 0 to 5 and m represents an integer of 1 or 2), or derivatives thereof at its carboxyl group(s) or their salts are included in the scope of the invention.

It is to be noted that for convenience the polyenepolycarboxylic acids represented by the above formula (1) (wherein n represents an integer of 0 to 5 and m represents an integer of 1 or 2), or derivatives thereof at their carboxyl group(s) or their salts will sometimes be referred to as "the compounds of the present invention" in the following description. Further, for simplification, the polyenepolycarboxylic acid of the above formula (1) wherein m=1 and n=0 will be referred to as "R0 compound"; the polyenepolycarboxylic acid of the above formula (1) wherein m=2 and n=0 as "S0 compounds"; the polyenepolycarboxylic acid of the above formula (1) wherein m=2 and n=1 as "S1 compound"; and the polyenepolycarboxylic acid of the above formula (1) wherein m=2 and n=2 as "S2 compound". Similarly, those R0, S0, S1 and S2 compounds in which two carboxyl groups bonded to adjacent carbon atoms are entirely bonded together to form an acid anhydride will simply be referred to as "R0 anhydride", "S0 anhydride", "S1 anhyd ride", and "S2 anhydride", respectively. The structural formulae of these compounds are shown below.

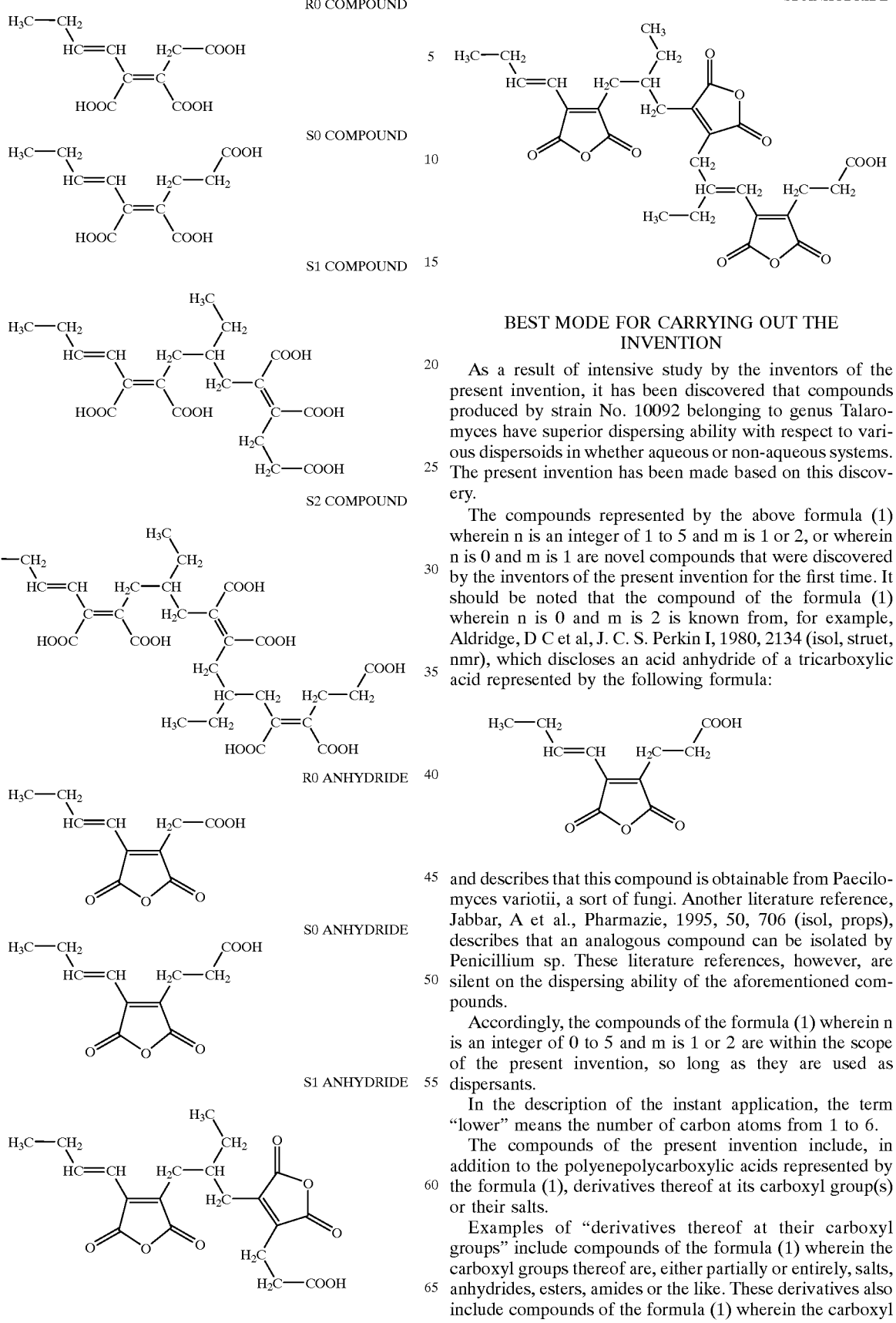

BEST MODE FOR CARRYING OUT THE INVENTION

As a result of intensive study by the inventors of the present invention, it has been discovered that compounds produced by strain No. 10092 belonging to genus Talaromyces have superior dispersing ability with respect to various dispersoids in whether aqueous or non-aqueous systems. The present invention has been made based on this discovery.

The compounds represented by the above formula (1) wherein n is an integer of 1 to 5 and m is 1 or 2, or wherein n is 0 and m is 1 are novel compounds that were discovered by the inventors of the present invention for the first time. It should be noted that the compound of the formula (1) wherein n is 0 and m is 2 is known from, for example, Aldridge, D C et al, J. C. S. Perkin I, 1980, 2134 (isol, struet, nmr), which discloses an acid anhydride of a tricarboxylic acid represented by the following formula:

and describes that this compound is obtainable from Paecilomyces variotii, a sort of fungi. Another literature reference, Jabbar, A et al., Pharmazie, 1995, 50, 706 (isol, props), describes that an analogous compound can be isolated by Penicillium sp. These literature references, however, are silent on the dispersing ability of the aforementioned compounds.

Accordingly, the compounds of the formula (1) wherein n is an integer of 0 to 5 and m is 1 or 2 are within the scope of the present invention, so long as they are used as dispersants.

In the description of the instant application, the term "lower" means the number of carbon atoms from 1 to 6.

The compounds of the present invention include, in addition to the polyenepolycarboxylic acids represented by the formula (1), derivatives thereof at its carboxyl group(s) or their salts.

Examples of "derivatives thereof at their carboxyl groups" include compounds of the formula (1) wherein the carboxyl groups thereof are, either partially or entirely, salts, anhydrides, esters, amides or the like. These derivatives also include compounds of the formula (1) wherein the carboxyl groups thereof are, either partially or entirely, in combination of them. Specifically, examples of such derivatives include compounds of the formula (1) wherein part of the carboxyl groups is an ester, while the rest is an anhydride. The above expression "their salts" means salts of the foregoing derivatives, examples of which include compounds of the formula (1) wherein part of the carboxyl groups is a derivative as above, while the rest is a salt.

The "salts" as stated above are any common non-toxic salts without any particular limitation to specific sorts thereof. Examples of such salts include alkali metal salts (such as sodium salts and potassium salts), alkali earth metal salts (such as calcium salts and magnesium salts), ammonium; salts, organic base salts (such as trimethylamine salts, triethylamine salts, pyridine salts, picoline salts, dicyclohexylamine salts and N,N'-dibenzylethylenediamine salts), and salts with amino acids (such as arginine salts, asparates and glutamates).

Examples of the "anhydrides" as stated above include those in which two carboxyl groups bonded to adjacent carbon atoms are combined into an acid anhydride group. An example of such an anhydride is shown below.

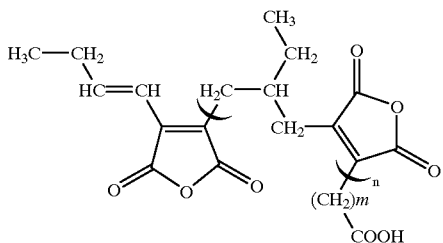

The "esters" as stated above include esterified carboxyl groups, and examples of preferred esters include alkyl esters including lower alkyl esters such as inethyl ester, ethyl ester, propyl ester, isopropyl ester, butyl ester, isobutyl ester, tertiary butyl ester, pentyl ester and hexyl ester.

The "amides" as stated above include amidated carboxyl groups, which may be condensed like a maleimide. Examples of such amides include lower alkylamides such as monomethylamide and monoethylamide; and arylamides such as monophenylamide, monobenzylamide and phenetylamide.

The "salts", "anhydrides", "esters" and "amides" described above may be prepared according to conventional methods.

The above "anhydrides" each may be prepared, for example, by a method such as to subject the polyenepolycarboxylic acids of the formula (1) to a dehydration reaction.

The above "esters" each may be prepared by a method such as to react the polyonopolycarboxylic acids of the formula (1) with an alcohol or as to subject acid anhydrides of the polyenepolycarboxylic acids to esterification reaction.

The above "amides" each may be prepared by a method such as to subject ammonium salts of the polyenepolyearboxylic acids represented by the formula (1) to a dehydration reaction, or to subject nitrile compounds of the polyenepolycarb oxylic acids to a saponification reaction, or to subject acid anhydrides or esters of the polyenepolycarboxylic acids or the Like to amidation reaction.

The S1 and S2 compounds of the foregoing compounds of the present invention have been confirmed to be extremely low toxic and safe compounds since they showed negativity in a mutagenicity test and no particular abnormality in a mouse acute toxicity test (oral administration: 2.0 g/kg).

Next, methods of obtaining the compounds of the present invention from a microorganism belonging to genus Talaromyces are described below.

First, a method of cultivating the microorganism is described. This microorganism, the characteristics of which will be described later, belongs to fungi, or what is commonly called "mold" (filamentous fungi) and, hence, generally known culture media for fungi may be used in cultivating the microorganism. Examples of such culture media include those comprising a carbon source, a nitrogen source, inorganic salts and a trace nutrient source. As the carbon source can be used glucose, xylose, fructose, sucrose, maltose, starch, oxidized starch, and hydrolyzed starch. As the nitrogen source can be used natural products such as corn steep liquor; inorganic nitrogen compounds such as sodium nitrate; and amino acids such as leucine and lysine. As the inorganic salts can be used calcium carbonate and magnesium sulfate or the like; and as the trace elements can be used iron sulfate or the like.

A culture medium to be used may be either a liquid medium or a solid medium, which is preferably subjected to shaking culture or aeration spinner culture. If the pH and temperature of such a culture medium under cultivation are adjusted to 3–8 and to 20–40° C., respectively, it is possible to obtain an effectively active components with higher productivity. It is recommended that the incubation period be three to five days, and a culture may. be obtained by a continuous fermentation as well as by a batch process.

The compounds of the present invention are obtained by extracting the culture thus obtained, followed by isolation or purification. Specifically, the culture obtained by the above method is separated into the culture solution and the fungal mass by filtration or centrifugal separation to afford a culture filtrate containing the compounds of the present invention. The culture filtrate is subjected to conventional extraction and isolation or purification processes, thus giving the compounds of the present invention. These extraction and isolation or purification processes are not particularly limited and can be appropriately selected from conventional processes. To isolate or purify the compounds of the present invention, for example, it is possible to adopt processes such as an acid treatment in which an acid such as a mineral acid or an organic acid is added to the culture filtrate, a treatment using an ion exchange resin, an adsorbing resin or the like, and a process using a dialysis membrane, an ultrafiltration membrane or gel permeation.

The compounds thus obtained are each treated by conventional methods to give derivatives thereof at their carboxyl group(s) or their salts. Derivatives, for example, esters or amides, of such a compound of the present invention can be obtained by subjecting a crude product resulting from concentration and evaporation to dryness of the aforementioned filtrate to a chemical reaction to give the derivatives such as esters or amides, followed by purification according to a conventional purification method adapted for fat-soluble substances. These derivatives may be hydrolyzed to give the compounds of the present invention and salts thereof. As to a series of these processes, reference may be made to methods described in examples to be described later.

The compounds (1), or derivatives thereof at their carboxyl group(s) or their salts thus obtained exhibit superior dispersing ability with respect to a wide range of organic and inorganic dispersoids in aqueous or non-aqueous systems and hence can be used as dispersants in various industrial fields such as coatings, pigments, inks, fiber, paper, cosmetic articles, foods, contrast media, paints, cement, concrete, rubber, plastics, ink jet, pharmaceuticals, agricultural chemicals, dyes, glazes, COM [Coal Oil Mixture (finely-divided coal)], photo graphic films, magnetic tapes, scale, heavy oil, and cleaning dispersants (lubricant oil additives).

Further, the compounds of the present invention also possess a chelating action. That is, the compounds of the present invention chelate with interfering metal ions thereby masking these metal ions. By making use of such an action, the compounds can be used as additives to detergents or dyes, and as stabilizers for foods, chemicals, cosmetic articles, and the like. Specifically, the compounds of the present invenion can find use in broad industrial fields such as metallic surface cleaning agents, bottle washing agents used in the food processing industry, glass instrument washing agents used in hospitals and like facilities, and dye-assist agents used in the dyeing industry.

Furthermore, the compounds of the present invention also possess a surface activity. By making use of such an activity, the compounds can be widely used in detergents for clothes, kitchen, hair, face and body, in emulsifying agents for cosmetic articles and agricultural chemicals, in anti static agents for clothes, and in like applications.

As to the amount of the dispersant of the present invention, a suitable amount range can appropriately be selected depending on the sort of dispersoid to be used or a like factor. Generally, addition of the dispersant in a range from 0.01 to 20 wt % to a dispersoid is preferable. The addition of the dispersant in an amount of less than 0.01 wt % would not result in a desired dispersing action. The addition of not less than 0.1 wt % of the dispersant is more preferable. On the other hand, the addition of more than 20 wt % of the dispersant would raise problems such as an occurrence of precipitation. The addition of not more than 10 wt % is more preferable.

Description will follow of microorganisms belonging to genus Talaromyces that can produce the compounds of the present invention. It should be noted that the following description is directed to the characteristics of strain No. 10092 of filamentous fungi isolated by the inventors of the instant application as a representative example but never intends to limit to this microorganism.

The above strain No. 10092 of filamentous fungi has been separated from soil collected at Ibusuki city, Kagoshima, Japan. This strain can widely grow on various culture media and form a colony with a color tone from yellowish white to light yellow. The strain formed many teleomorphg (ascocarps) and a few anamorphs (conidium structures) on a culture medium. The teleomorphs were each a spherical ascocarp in an orange color covered with undifferentiated hyphae in which asci lay scattered. The ascospore thereof was a colorless, single cell, wide elliptic and was observed to have a ridge on an equatorial surface. On the other hand, the anamorphs each comprised a single conidiogenous cell or broom-like conidiophore and formed chain-linked conidia each shaped spherical and comprised of a single cell. The mycological characteristics of the strain are as follows.

The attributes of cultures resulting on various agar culture media are summarized in Tables 1 to 3.

It should be noted that the data in Table 1 were those observed after incubation at 25° C. for seven days from inoculation. The color tones were described based on Methuen Handbook of Colour (Komerup, A. and J. H. Wanscher, 3rd ed., 525p., Methuen, London, 1978).

Further, the data in Tables 2 and 3 were those observed after incubation at 25° C. for 14 days from inoculation. The color tones were observed and determined in the same manner as in Table 1.

TABLE 1

| Culture medium | Culture attribute | |
|---|---|---|
| Malt-extracted agar* | Growth | 6.2–7.0 cm in diameter, circular |
| | Face | flat, from felt-like to granular state, a small quantity of anamorphs formed, from white (1A1) or yellowish white (3A2) to light yellow (3A3) |

TABLE 1-continued

| Culture medium | Culture attribute | |
|---|---|---|
| | Reverse face | from yellow (3A6) to grayish yellow (3B6), a soluble yellow dye produced |
| Yeast extract-added Czapek agar* | Growth | 4.7–5.2 cm in diameter, circular |
| | Face | flat, felt-like state, radial grooves formed, neither teleomorph nor anamorph formed, from white (1A1) or yellowish white (2A2) to light yellow (2A3) |
| | Reverse face | yellowish white (4A2) or grayish yellow (4B4) |
| G25N agar* | Growth | 0.7–1.3 cm in diameter, circular |
| | Face | bulged, fluff-like state, neither teleomorph nor anamorph formed, white (1A1) |
| | Reverse face | white (1A1) |

Note on asterisk*:
the compositions of the malt-extracted agar, yeast extract-added Czapek agar and G25N agar were in conformity with the monograph by Pitt (Pitt, J. I., The genus Penicillium and its teleomorphic states Eupenicillium and Talaromyces, Academic Press, London, 1979).

TABLE 2

| Culture medium | Culture attribute | |
|---|---|---|
| Malt-extracted agar | Growth | broadly expansive, circular, 8.0 cm or more in diameter |
| | Face | flat, from felt-like to granular state, abundance of teleomorphs and a small quantity of anamorphs formed, from yellowish white (2A2) to light yellow (3A3) |
| | Reverse face | from yellow (3A6) to grayish yellow (3B6), a soluble yellow dye produced |
| Potato dextrose agar (Difco 0013) | Growth | broadly expansive, circular, 8.0 cm or more in diameter |
| | Face | flat, from felt-like to fluff-like or granular state, a sector formed, abundance of teleomorphs formed but no anamorph observed, from yellowish white (3A2) to light yellow (3A3) with the sector in yellowish white (4A2) |
| | Reverse face | from yellowish brown (5D5) to brown (6E5) with the sector in bright yellow (4A4) |
| Czapek agar** | Growth | broadly expansive, circular, 8.0 cm or more in diameter |
| | Face | flat, felt-like state, teleomorphs formed but immature, a small quantity of anamorphs formed, from light yellow (3A3) to bright yellow (3A4) at a central portion, yellowish white (2A2 to 4A2) at a peripheral portion, and from light orange (5A3) to bright orange (5A4) at an intermediate portion, an infusion in light orange produced |
| | Reverse face | brown (5E6 to 6E7) with a peripheral portion in yellow (3A6) to grayish yellow (3B6), a soluble light yellow dye produced |
| Sabouraud dextrose agar (Difco 0190) | Growth | broadly expansive, circular, 8.0 cm or more in diameter |
| | Face | flat, felt-like state, teleomorphs formed but immature, no anamorph observed, from white (1A1) to yellowish white (2A2) with a central portion in light yellow (2A3) |
| | Reverse face | from yellow (3A7) to reddish yellow (4B7), a soluble yellow dye produced |

Note on asterisks**:
the composition of the Czapek agar was in conformity with the JCM catalog (Nakase, T., 5th ed., 503 p., Japan Collection of Microorganisms and Life Science Research Information Section of the Institute of Physical and Chemical Research, Saitama, 1992).

TABLE 3

| Culture medium | Culture attribute | |
|---|---|---|
| Emerson Yp Ss Agar (Difco 0739) | Growth | broadly expansive, circular, 8.0 cm or more in diameter |
| | Face | flat, felt-like state with a peripheral portion in granular state, abundance of teleomorphs and anamorphs formed, from yellowish white (4A2) to light yellow (4A3) with the peripheral portion in yellowish white (1A2) to light yellow (1A3) |
| | Reverse face | light yellow (3A3 to 4A3) |
| Corn meal agar (Difco 0386) | Growth | broadly expansive, circular, 8.0 cm or more in diameter |
| | Face | flat, hyphae buried, thin, partially powdery state, abundance of teleomorphs and a small quantity of anamorphs formed, white (1A1) with ascocarps in yellowish white (3A2) |
| | Reverse face | white (1A1) with ascocarps in yellowish white (3A2) |
| MY20 agar** | Growth | broadly expansive, circular, 8.0 cm or more in diameter |
| | Face | flat, from felt-like to fluff-like state, teleomorphs formed but immature, no anamorph observed, from yellowish white (3A2) to light yellow (3A3) with a peripheral portion in yellowish white (1A2) to light yellow (1A3) |
| | Reverse face | reddish yellow (4B7) to grayish yellow (4C7), a soluble yellow dye diffused |
| Oatmeal agar | Growth | broadly expansive, circular, 8.0 cm or more in diameter |
| | Face | flat, felt-like to fluff-like state, radial grooves and a sector formed, teleomorphs formed but immature, anamorphs also formed, from yellowish white (4A2) to bright yellow (4A4) with a central portion in white (1A1) and the sector in light yellow (2A3) to bright yellow (2A4) |

Note on asterisks**:
the composition of the MY20 agar was in conformity with JCM catalog (Nakase, T., 5th ed., 503 p., Japan Collection of Microorganisms and Life Science Research Information Section of the Institute of Physical and Chemical Research, Saitama, 1992).

From these Tables, considerations can be given as follows.

The foregoing strain was rapidly cultivated in the yeast extract-added Czapek agar culture medium, and after incubation at 25° C. for seven days, it formed a circular colony having a diameter of 4.7 to 5.2 cm. The face of this colony was flat and felt-like, and formed with radial grooves. The color tone of the colony was white or yellowish white to light yellow, and that of the reverse face of the colony was yellowish white or grayish yellow. Neither teleomorph nor anamorph was observed.

In the case of cultivation in the malt-extracted agar culture medium, a colony was obtained more rapidly than in the above culture medium, and the size of the colony cultivated under the same condition as above reached 6.2 to 7.0 cm in diameter. This colony expanded circularly with its face being flat, in a felt-like to granular state and in a color tone from white or yellowish white to light yellow. The reverse face of the colony exhibited a color tone from yellow to grayish yellow and diffused a soluble yellow dye in the culture medium. On this culture medium was formed a small quantity of anamorphs. When the cultivation in the malt-extracted agar culture medium was conducted for two weeks, the resulting colony expanded to have a diameter of 8 cm or more, as noted in Table 2, and reached a wall surface of the Petri dish. The face of this colony was flat and in a felt-like to granular state, and formed a small quantity of anamorphs as well as abundance of teleomorphs. The colony exhibited a color tone from yellowish white to light yellow, and the reverse face thereof exhibited a color tone from yellow to grayish yellow and diffused a soluble yellow dye in the culture medium.

The morphological characteristics of the strain were determined based on the results of culture on an LCA agar culture medium (Miura culture medium) developed by Miura and Kudo (Miura, K. and M. Kudo: Trans. Mycol. Soc. Japan, 11: 116–118, 1970). As a result, there were observed abundant teleomorphs (ascocarps) and anamorphs (conidium structures).

These ascocarps were superficially present and independent, each shaped spherical to subspherical with a diameter of 350 $\mu$m at the maximum, and of the non-ostiolate form. The surface of each ascocarp was covered with interwoven hypha network and exhibited a color tone from yellowish white to orange. Within each ascocarp were scattered asci which were each evanescent, subspherical to elliptic, and 7 to 10 $\mu$m in diameter, and which each had eight ascospores therein. These ascospores exhibited a color tone from colorless to light orange, and each had a somewhat coarse surface, a single cell, and a wide elliptic to lens shape. Each of the ascospores further had a single ridge on an equatorial surface and a size of 3 to 4.5 $\mu$m×2.5 to 3 $\mu$m.

On the other hand, the conidium structure was of the phialo type in which conidia were formed as linked from phialides. These phialide8 generated as branching of aerial or substrate mycelia, or three to five such phialides were formed at the tip of a broomlike conidiophore. They were colorless and had smooth surfaces, pen-tip shapes, and a size of 13 to 18 $\mu$m×1.5 to 3.5 $\mu$m as a mononematous or 8 to 14 $\mu$m×1.5 to 3.5 $\mu$m as a verticillate. Each of the conidia was colorless an d had a smooth surface, a single cell, a spherical to wide elliptic or oval shape, and a size of 2 to 4 (or to 5) $\mu$m×2 to 3.5 $\mu$m. A vegetative hypha had a smooth surface and a septal wall, and was colorless and branching. The hypha cell was cylindrical and 1.5 to 6.5 $\mu$m wide, but any chlamydospore was not formed.

Examination of the foregoing strain as to its optimum temperature for growth with use of a potato dextrose agar culture medium (available from NISSUI SEIYAKU) proved that the strain could grow within a temperature range between 7° C. and 40° C., and that its optimum temperature for growth was 29° to 34° C.

When the foregoing mycological characteristics were compared to the fungi classification standard by von Arx (J. A. von Arx: The Genera of Fungi-Sporulating in Pure Culture. 3rd ed., J. Cramer, Vaduz, 1974) and the monograph by Pitt (Pitt, J. I., The genus Penicillium and its teleomorphic states Eupenicillium and Talaromyces, Academic Press, London, 1979), the strain No. 10092 was considered to belong to genus Talaromyces (Talaromyces C. R. Benji. 1955) of Plectomycetes. Thus, this strain was identified as one strain of genus Talaromyces and named "Talaromyces sp. No. 10092". It should be noted that this strain has been deposited to National Institute of Bioscience and Human-Technology, Agency of Industrial Science and Technology as an International Depositary Authority established under the Budapest Treaty, with a deposit No. FERM BP-6250 (Date of acceptance of deposit: Feb. 9, 1998).

Hereinafter, the present invention will be described in detail by way of examples thereof. It should be noted that the following examples are not limitative of the present invention and that modifications in practice which may be made within the range not departing from the context of the description are all included in the technical scope of the present invention.

The gtrain No. 10092 was cultivated according to the methods employed in the following culture examples 1 to 5.

CULTURE EXAMPLE 1

Aeration Spinner Culture Method (Case 1)

① Pre-cultivation 1

A culture medium 1 (60 mL) of the following composition was placed into a flask of 225 mL cap., and after inoculation of a seed fungus with use of a slant, a culture was incubated at 25° C. for three days.

The composition of culture medium 1:

| | |
|---|---|
| Glycerin | 2% |
| Sucrose | 2% |
| FERMA MEDIA | 2% |
| Dried yeast | 1% |
| Peptone | 1% |
| $KH_2PO_4$ | 0.1% |
| Tween 80 | 0.1% |

② Pre-cultivation 2

A culture medium 2 (140 mL) of the following composition was placed into a flask of 500 mL cap., then a fungus-carrier liquid (2.4 mL) obtained in pre-cultivation 1 was inoculated, and a culture was incubated at 25° C. for three lays.

The composition of culture medium 2:

| | |
|---|---|
| Corn starch | 3% |
| Corn steep liquor | 3% |
| $CaCO_3$ | 0.2% |
| adjusted to pH 7 with NaOH | |

③ Main cultivation

Into a jar of 30 L cap. was placed the culture medium 2 (24 L), to which, after sterilization, the fungus-carrier liquid (480 mL) of the pre-cultivation 2 was added, and the resultant was incubated at 25° C. for four days while being stirred at 300 revolutions under aeration using 20 L per minute of sterilized air. After the cultivation, the culture medium was admixed with a filter aid ("RADIOLIGHT" produced by SHOWA-CHEMICAL INDUSTRY: filter medium for food additives, diatomaceous earth) and then separated into a filtrate and a fungal mass with use of a filter press ("TFP-6-12 FILTER PRESS" manufactured by TOKYO ENGINEERING). As a result, a filtrate (40 L: 1.7% dry solids content) was obtained from three 30 L cap. jars.

CULTURE EXAMPLE 2

Aeration Spinner Culture Method (Case 2)

In this culture example, the amounts of the culture medium and fungus-carrier liquid were increased 10 times as large as those used in culture example 1 to cultivate the foregoing strain.

Specifically, the strain was cultivated in the same manner as in culture example 1 except that in the main cultivation of culture example 1 the culture medium 2 (240 L) was placed into a jar of 300 L cap., sterilized, and admixed with the fungus-carrier liquid (4.8 L) of the pre-cultivation 2 and the resultant was incubated while being stirred at 150 revolutions under aeration using 200 L per minute of sterilized air. As a result, a filtrate (100 L: 1.4% dry solids content) was obtained.

Unlike the foregoing culture examples 1 and 2 employing the aeration spinner culture, the following culture examples 3 to 6 employed the shaking culture.

CULTURE EXAMPLE 3

Shaking Culture Method (Case 1)

The culture medium 2 (60 mL) was placed into a glass conical flask of 225 mL cap. and thereafter a fungus-carrier liquid (1.2 mL) obtained by pre-cultivation according to culture example 1 was added to the culture medium 2, followed by incubation at 25° C. for four days under shaking at 1500 rpm. The culture thus obtained was admixed with RADIOLIGHT as a filter aid and then filtered by a Buchner funnel, to give a filtrate (40 mL: 1.25% dry solids content).

CULTURE EXAMPLE 4

Shaking Culture Method (Case 2)

A filtrate (40 mL: 1.25% dry solids content) was obtained in the same manner as in culture example 3 except for the use of a culture medium 3 of the composition shown in Table 4 instead of the culture medium 2.

TABLE 4

| Ingredient | Culture medium 3 | Culture medium 4 | Culture medium 5 |
|---|---|---|---|
| Xylose | — | 30.0 | — |
| Sucrose | 30.0 | — | — |
| Fructose | — | — | 50.0 |
| Calcium carbonate | 0.01 | 5.0 | 0.2 |
| Sodium nitrate | 3.0 | 2.0 | 3.0 |
| Dipotassium phosphate | 1.0 | 1.0 | 1.0 |
| Magnesium sulfate | 0.5 | 0.5 | 0.5 |
| Potassiumchloride | 0.5 | — | 0.5 |
| Iron sulfate | 0.01 | 0.01 | 0.01 |
| Leucine | — | 0.6 | — |
| Lysine | — | 0.3 | — |
| pH | 7.3 ± 0.2 | 7.3 ± 0.2 | 7.3 ± 0.2 |

*Note:
the amount of each ingredient is in the unit of g/L.

CULTURE EXAMPLE 5

Shaking Culture Method (Case 3)

A filtrate (40 mL: 1.25% dry solids content) was obtained in the same manner as in culture example 3 except for the use of a culture medium 4 of the composition shown in Table 4 instead of the culture medium 2.

CULTURE EXAMPLE 6

Shaking Culture Method (Case 4)

A filtrate (40 mL: 1.25% dry solids content) was obtained in the same manner as in culture example 3 except for the use of a culture medium 5 of the composition shown in Table 4 instead of the culture medium 2.

Next, the culture filtrate was subjected to purification or isolation according to the following preparation examples to provide the compounds of the present invention.

It should be noted that the culture filtrate was confirmed to contain a pentasodium salt of S1 compound and a heptasodium salt of S2 compound by the analysis under the following conditions.

[HPLC Analysis Conditions]

Column: TSKgel ODS-80TsQA
 (4.6 φ×250 mm, manufactured by TOSOH)

Column temperature: 40° C.

Mobile phase:
   phosphoric acid buffer solution*:methanol=65:35 (analysis condition 1)
   phosphoric acid buffer solution*:methanol=60:40 (analysis condition 2)

Flow velocity: 1.0 mL/min

Detection: UV 260 nm

Note on asterisk*: 20 mM of an $Na_2HPO_4$ aqueous solution (containing 5 mM of tetrabutylammonium bromide) adjusted to pH 7.5 with a phosphoric acid aqueous solution (prepared by diluting 1 mL of phosphoric acid with 10 mL of water).

The results of the analysis under the analysis conditions 1 and 2 are shown in Tables 5 and 6, respectively.

TABLE 5

|  | Retention time (peak area) | |
| --- | --- | --- |
| Filtrate | 9.5 (327953) | 17.4 (310786) |
| Pentasodium salt of S1 compound | 9.3 (685634) | |
| Heptasodium salt of S2 compound | | 17.2 (300316) |
| Filtrate + pentasodium salt of S1 compound | 9.3 (1034918) | 17.4 (302496) |
| Filtrate + heptasodium salt of S2 compound | 9.5 (332875) | 17.2 (607650) |

TABLE 6

|  | Retention time (peak area) | |
| --- | --- | --- |
| Filtrate | 5.1 (321296) | 6.7 (488487) |
| Pentasodium salt of S1 compound | 5.1 (599122) | |
| Heptasodium salt of S2 compound | | 6.6 (611893) |
| Filtrate + pentasodium salt of S1 compound | 5.2 (1011628) | 6.9 (529522) |
| Filtrate + heptasodium salt of S2 compound | 5.2 (353880) | 6.7 (1051828) |

Comparison between the retention times until respective peaks proved that in the filtrate were present both a pentasodium salt of S1 compound in which all the carboxyl groups in S1 compound were substituted with sodium salt and a heptasodium salt of S2 compound in which all the carboxyl groups in S2 compound were substituted with sodium salt. Since there were slight differences between the retention times until respective peaks, equivalent weights of the filtrate and the salt of each of S1 and S2 compounds were mixed as [filtrate+pentasodium salt of S1 compound] and [filtrate+heptasodium salt of S2 compound] and injected into a column to test how much the sum of peak areas was.

The equivalent weight mixtures each exhibited an increase in respective peak and a peak area which was equal to the sum of the peak areas of the two. The same result was obtained even when the mobile phase was changed.

PREPARATION EXAMPLE 1

Isolation of the Compounds of the Present Invention from the Culture Filtrate

In this preparation example, the culture filtrate obtained in the above culture example was purified to isolate the compounds of the present invention.

Specifically, the culture filtrate (5.1 L) obtained in culture example 2 was adjust to pH 3, and then extracted with ethyl acetate (7.6 L). The extract thus obtained was dried over anhydrous magnesium sulfate and then the solvent was removed under reduced pressure to give a transparent brown oily substance (37 g).

This oily substance was fractionated with an HPLC under the following conditions, resulting in separation into a fore-eluted fraction of S1 anhydride and an eluted fraction containing S1 anhydride and S2 anhydride.

[HPLC Fractionation Conditions]

Column: ODS column, 50 mm in diameter and 250 mm in length, manufactured by YMC

Column temperature: room temperature

Mobile phase:
   acetonitrile:phosphoric acid buffer solution=6:4 (composition of the phosphoric acid buffer solution: 6.53 g of $KH_2PO_4$, 1.18 g of $H_3PO_4$, and 3 L of water)

Flow velocity: 50 mL/min

Detection: UV 210 nm

Subsequently, each of the fore-eluted fraction of S1 anhydride and the eluted fraction containing S1 and S2 anhydrides was distilled under reduced pressure to remove acetonitrile, then a resulting aqueous layer was subjected to extraction with ethyl acetate, and the resulting extract was dried over anhydrous magnesium sulfate, followed by removal of ethyl acetate under reduced pressure to afford a fore-eluted fraction of S1 anhydride (3.9 g), the S1 anhydride (7.7 g) and the S2 anhydride (13.7 g).

Of these, 850 mg of the fore-eluted fraction of S1 anhydride was further fractionated with an HPLC under the following conditions, to give an eluted fraction containing S0 anhydride.

[HPLC Fractionation Conditions]

Column: ODS column, 50 mm in diameter and 250 mm in length, manufactured by YMC

Column temperature: room temperature

Mobile phase:
   acetonitrile:phosphoric acid buffer solution=4:6 (composition of the phosphoric acid buffer solution: 6.53 g of $KH_2PO_4$, 1.18 g of $H_3PO_4$, and 3 L of water)

Flow velocity: 50 mL/min

Detection: UV 210 nm

Subsequently, the eluted fraction containing S0 anhydride was distilled under reduced pressure to remove acetonitrile, then a resulting aqueous layer was subjected to extraction with ethyl acetate, and the resulting extrac was dried over anhydrous magnesium sulfate, followed by removal of ethyl acetate under reduced pressure to afford S0 anhydride (70 mg). The $^1$H-NMR data of this substance were confirmed to agree to the values shown in the literature references: Aldridge, D C et al., J. C. S. Perkin I, 1980, 2134; Jabbar, A et al., Pharmazie, 1995, 50, 706.

S1 and S2 anhydrides are colorless transparent oily substances characterized by the following properties and instrumental analysis data.

① Property and Instrumental Analysis Data of S1 Anhydride a) Property: a colorless transparent oily substance, b) Molecular formula: $C_{20}H_{22}O_8$; ESI mass spectrum (m/z): 389 $(M-H)^-$.

c) Ultraviolet absorption spectrum (acetonitrile): $\lambda_{max}$ (nm): 255, 312.

d) Infrared absorption spectrum (neat, NaCl plate): $\nu_{max}$: 3100–2600, 2970, 1815, 1770, 1705, 1640, 1430, 1355, 1265, 965, 920 $cm^{-1}$.

e) $^1$H-NMR spectrum (CDCl$_3$): δ (integrated value, multiplicity): 7.28 (1H, dt, J=15.8, 6.6 Hz), 6.23 (1H, dt, J=15.8, 1.5 Hz), 2.90–2.70 (4H, m), 2.62–2.16 (7H, m), 1.42–1.26 (2H, m), 1.12 (3H, t, J=7.4 Hz), 0.98 (3H, t, J=7.0 Hz) ppm.

f) $^{13}$C-NMR spectrum (CDCl$_3$): δ (multiplicity): 177.3 (s), 166.2 (s), 165.5 (s), 165.2 (s), 164.1 (8), 150.6 (d), 144.3 (s), 143.5 (8), 138.5 (s), 136.8 (8), 115.9 (d), 38.2 (d), 30.8 (t), 28.7 (t), 28.2 (t), 27.8 (t), 26.7 (t), 19.8 (t), 12.4 (q), 10.7 (q) ppm.

② Property and instrumental analysis data of S2 anhydride a) Property: a colorless transparent oily substance.

b) Molecular formula: C$_{29}$H$_{32}$O$_{11}$; ESI mass spectrum (m/z): 555 (M-H)$^-$.

c) Ultraviolet absorption spectrum (acetonitrile): ν$_{max}$ (nm): 258, 313.

d) Infrared absorption spectrum (neat, NaCl plate): ν$_{max}$: 3100–2600, 2970, 1816, 1770, 1705, 1640, 1430, 1350, 1265, 965, 925 cm$^{-1}$.

e) $^1$H-NMR spectrum (CDCl$_3$); δ (integrated value, multiplicity); 7.28 (1H, dt, J=15.8, 6.7 Hz), 6.23 (1H, dt, J=15.8, 1.5 Hz), 2.70–2.90 (4H, m), 2.63–2.18 (12H, m), 1.37–1.26 (4H, m), 1.11 (3H, t, J=7.4 Hz), 0.97 (6H, t, J=7.0 Hz ) ppm.

f) $^{13}$C-NMR spectrum (CDCl$_3$): δ (multiplicity): 177.1 (s), 166.3 (s), 165.7 (s), 165.6 (s), 165.5 (s), 165.2 (s), 164.0 (s), 150.7 (d), 144.4 (s), 144.2 (s), 144.0 (s), 143.7 (s), 138.6 (s), 136.7 (s), 115.9 (d), 38.0 (d), 37.7 (d), 30.7 (t), 29.0 (t), 28.9 (t), 28.7 (t), 28.2 (t), 27.5 (t), 26.8 (t), 26.7 (t), 19.8 t)., 12.4 (q), 10.7 (2c:q) ppm.

PREPARATION EXAMPLE 2

Preparation of Sodium Salts of S1 and S2 Compounds

Next, S1 anhydride (206 mg) and S2 anhydride (199 mg) isolated in preparation example 1 were each suspended in water (100 mL), then to the resulting suspension was added dropwise an aqueous solution of 0.1 N sodium hydroxide under stirring until the pH value of the suspension assumed 7 to cause neutralization and dissolution, and the resulting solution was concentrated under reduced pressure and evaporated to dryness, to afford a pentasodium salt of S1 compound (304 mg) and a heptasodium salt of S2 compound (290 mg) each in a powdery state. The properties and instrumental analysis data of these salts are as follows.

③ Property and Instrumental Analysis Data of the Pentasodium Salt of S1 Compound a) Property: a colorless powdery substance.

b) Infrared absorption spectrum (nujol, NaCl plate): ν$_{max}$: 3700–2600, 2960, 1660, 1630, 1560, 1400 cm$^{-1}$.

c) $^1$H-NMR spectrum (D$_2$O): δ (integrated value, multiplicity): 6.38 (1H, d, J=15.8 Hz), 5.87 (1H, dt, J=15.8, 6.6 Hz), 2.54–2.10 (10H, m), 1.53 (1H, m), 1.33 (2H,m), 1.00 (3H, t, J=7.4 Hz), 0.86 (3H, t, J=7.0 Hz) ppm.

d) $^{13}$C-NMR spectrum (D$_2$O): δ (multiplicity): 185.5 (s), 182.0 (s), 181.8 (s), 181.7 (s), 180.8 (s), 143.0 (s), 141.0 (d), 140.4 (s), 139.8 (s). 135.2 (s), 126.6 (d), 41.3 (d), 39.1 (t), 36.4 (t), 3 5.3 (t), 29.7 (t), 28.8 (t), 27.4 (t), 15.7 (q), 12.9 (q) ppm.

④ Property and Instrumental Analysis Data of the Heptasodium Salt of S2 Compound a) Property: a colorless powdery substance.

b) Infrared absorption spectrum (nujol, NaCl plate): ν$_{max}$: 3700–2600, 2960, 1660, 1630, 1565, 1400 cm$^{-1}$.

c) $^1$H-NMR spectrum (D$_2$O): δ (integrated value, multiplicity): 6.38 (1H, d, J=15.8 Hz), 5.86 (1H, dt, J=15.8, 6.7 Hz), 2.53–2.19 (14H, m), 1.60–1.18 (6H, m), 1.01 (3H, t, J=6.4 Hz), 0.86 (3H, t, J=7.0 Hz), 0.84 (3H, t, J=7.0 Hz) ppm.

d) $^{13}$C-NMR spectrum (D$_2$O): δ (multiplicity): 185.4 (s), 182.3 (2C:s), 181.9 (2C:s), 181.7 (s), 181.0 (s), 142.7 (s), 140.9 (d), 140.8 (s), 140.7 (s), 140.1 (a), 140.0 (s), 135.4 (s), 126.6 (d), 41.4 (d), 40.6 (d), 39.1 (t), 37.1 (2C:t), 36.4 (t), 35.3 (t), 29.6 (t), 28.8 (t), 27.1 (2C:t), 15.8 (q), 12.9 (q), 12.8 (q) ppm.

PREPARATION EXAMPLE 3

Method of Preparing a Pentamethyl Ester of S1 Compound and a Heptamethyl Ester of S2 Compound The fermentation filtrate (100 mL, pH=6.2) obtained in culture example 2 was stirred at room temperature and to this filtrate was added an aqueous solution of 1N acetic acid in small portions. Precipitate began to deposit at the time when the pH of the filtrate assumed 4.2. To the filtrate was further added the acetic acid aqueous solution until the pH o f the filtrate assumed 3 (about 350 mL), and then zeolite (1 g) was added, followed by filtration. To a solid matter (1.45 g) resulting from the filtration was added distilled water (50 mL), and the resultant was stirred to give a suspension (pH=3.6), which was then neutralized (pH=7) with an aqueous so ution of 1N sodium hydroxide and stirred at room temperature for an hour, followed by filtration to remove insolubles. To the filtrate thus obtained was added an aqueous solution of 1N acetic acid to, adjust to pH=3 (about 200 mL), and resulting precipitate was extracted with methylene chloride. A resulting methylene chloride layer was dried over magnesium sulfate, distilled under reduced pressure to remove the solvent, admixed with toluene to azeotropically remove acetic acid, thereby affording an acid extract (1.4 g).

Subsequently, the acid extract (80 mg) was dissolved in a mixture of ether (2 mL) and methanol (1 mL), and a diazomethane ether solution was added in small portions to the resulting solution under cooling with ice until the reaction liquid became yellow. The diazomethane ether solution used had been prepared by: adding 40% (w/w) potassium hydroxide (10 mL) to ether (15 mL) and cooling the mixture with ice; thereafter adding N-methyl-N-nitrosourea (0.5 g) in small portions to the mixture until the ether layer was confirmed to become yellow; and separating the ether layer, followed by drying over potassium hydroxide granules.

In turn, this solution was allowed to undergo a reaction at room temperature for 16 hours. After the reaction, the solvent was removed under reduced pressure to give a crude product, which was then separated using 5 pieces of preparative TLC plate [normal phase silica gel, 20 cm×20 cm, developing solvent (hexane:ethyl acetate=1:2)], to afford a methylated S1 compound (20. 5 mg) and a methylated S2 compound (16.8 mg). The $^1$H-NMR and IR data of these compounds were as shown below. From these data, the compounds thus obtained were confirmed to be respective derivatives of S1 and S1 compounds in which all the carboxyl groups of S1 and S2 compounds were methyl-esterified.

⑤ Pentamethyl Ester of S1 Compound a) $^1$HNMR spectrum (CDCl$_3$): δ (integrated value, multiplicity): 6.31 (1H, dt, J=15.8, 1.3 Hz), 6.01 (1H, dt, J=15.8, 6.6 Hz), 3.83 (3H, s), 3.75(3H, s), 3.72 (3H, 5), 3.71 (3H, s), 3.68 (3H, s), 2.69 (2H t, J=8.2 Hz), 2.44 (2H, t, J=8.2 Hz), 2.35–2.48 (3H, m), 2.30 (1H, dd, J=13.9, 6.9 Hz), 2.24

(2H, ddq, J=7.4, 6.6, 1.3 Hz) 1.63 (1H, hep, J=6.9 Hz), 1.25–1.35 (2H, m), 1.05 (3H, t, J=7.4 Hz), 0.91 (3H, t, J=7.3 Hz) ppm.

b) Infrared absorption spectrum (neat, NaCl plate): $v_{max}$: 1716, 1280 cm$^{-1}$.

⑥ Heptamethyl Ester of S2 Compound a) $^1$H-NMR spectrum (CDCl$_3$): δ (integrated value, multiplicity): 6.31 (1H, dt, J=15.8, 1.3 Hz), 6.01 (1H, dt, J=15.8, 6.6 Hz), 3.83 (3H, a), 3.74(3H, s), 3.73 (3H, s), 3.72 (6H, bs), 3.70 (3H, s), 3.67 (3H, s), 2.68 (2H t, J=7.7 Hz), 2.44 (2H, t, J=7.7 Hz), 2.2–2.42, (10H, m), 1.49–1.59 (2H, m), 1.23–1.33 (4H, m), 1.04 (3H, t, J=7.4 Hz), 0.89 (3H, t, J=7.4 Hz), 0.87 (3H, t, J=7.4 Hz) ppm.

b) Infrared absorption spectrum (neat, NaCl plate): $v_{max}$: 1731, 1264 cm$^{-1}$.

PREPARATION EXAMPLE 4

Method of Preparing p-Bromobenzylamide of S2 Anhydride

Diphenylphosphoryl chloride (110 mg) and N-methyl morpholine (81 mg) were added to a solution of S2 anhydride (224 mg) in acetonitrile (2 mL) under ice-cooling, followed by stirring for two hours. To the solution were further added p-bromobenzylamine hydrochloride (89 mg) and N-methyl morpholine (40 mg) under ice-cooling, and the resultant was allowed to undergo a reaction for one hour under ice-cooling and for two hours at room temperature. This reaction mixture was poured into water, extracted with ethyl acetate, washed with water, and dried over sodium sulfate. A crude product obtained by removing the solvent under reduced pressure was purified with a silica gel column chromatography and eluted with a mixture of hexane and ethyl acetate [1:1 (v/v)]. The solvent of the eluted fraction containing the desired product was removed under reduced pressure to a fford p-bromobenzylamide of S2 anhydride (193 mg). The $^1$H-NMR data of this compound were as shown below. From these data, the compound thus obtained was confirmed to be a derivative in which a carboxyl group of S2 anhydride was p-bromobenzylamidated.

$^1$H-NMR (D$_2$O): δ (integrated value, multiplicity): 7.43 (2H, d), 7.29 (1H, dt), 7.09 (2H, d), 6.20 (1H, dt), 5.88 (1H, t), 4.30 (2H, d), 2.81 (2H, t), 2.22–2.63 (14H, m), 1.22–1.37 (4H, m), 1.12 (3 H, t), 0.97 (6H, t) ppm.

PREPARATION EXAMPLE 5

Method of Preparing p-Nitrobenzylamide of S2 Anhydride

Diphenylphosphoryl acid chloride (79 mg) and N-methyl morpholine (60 mg) were added to a solution of S2 anhydride (163 mg) in acetonitrile (2 mL) under ice-cooling, followed by stirring for two hours. To the solution were further added p-nitrobenzylamine hydrochloride (55 mg) and N-methyl morpholine (30 mg) under ice-cooling, and the resultant was allowe d to undergo a reaction for one hour under ice-cooling and for two hours at room temperature. This reaction mixture was poured into water, extracted with ethyl acetate, washed with water, and dried over sod ium sulfate. A crude product obtained by removing the solvent under reduced pressure was purified with a silica gel column chromatography and eluted with ethyl acetate. The solvent of the eluted fraction containing the desired product was removed under reduced pressure to afford p-nitrobenzylamide of S2 anhyd ride (180 mg). The $^1$-NMR data of this compound were as shown below. From these data, the compound thus obtained was confirmed to be a derivative in which a carboxyl group of S2 anhydride was p-nitrobenzylamidated.

$^1$H-NMR (D$_2$O): δ (integrated value, multiplicity): 8.16 (2H, d), 7.40 (2H, d), 7.27 (1H, dt), 6.20 (1H, dt), 6.14 (1H, t), 4.48 (2H, d), 2.81 (2H, t), 2.18–2.69 (14H, m), 1.22–1.37 (4H, m), 1.12 (3H, t), 0.97 (6H, t) ppm.

PREPARATION EXAMPLE 6

Method of Preparing Cyclohexrlamide of S2 Anhydride

Diphenylphosphoryl acid chloride (110 mg) a nd N-methyl morpholine (57 mg) were added to a solution of S2 anhydridede (156 mg) in acetonitrile (2 mL) under ice-cooling, followed by stirring for two hours. To the solution were further added cyclohexylamine (28 mg) and N-methyl morpholine (28 mg) under ice-cooling, and the resultant was allowed to undergo a reaction for one hour under ice-cooling and for two hours at room temperature. This reaction mixture was poured into water, extracted with ethyl acetate, washed with water, and dried over sodium sulfate. A crude product obtained by removing the solvent under reduced pressure was purified with a silica gel column chromatography and eluted with a mixture of hexane and ethyl acetate [1:2 (v/v)]. The solvent of the eluted fraction containing the desired product was removed under reduced pressure to afford cyclohexylamide of S2 anhydride (10 mg). The $^1$H-NMR data of this compound were as shown below. From these data, the compound thus obtained was confirmed to be a derivative in which a carboxyl group of S2 anhydride was cyclohexylamidated.

$^1$H-NMR (D$_2$O): δ (integrated value, multiplicity): 7.31 (1H, dt), 6.22 (1H, dt), 5.37 (d, 1H), 3.66 (1H, m), 2.78 (2H, t), 2.05–2.61 (14H, m), 1.50–1.95 (10H, m), 1.22–1.37 (4H, m), 1.12 (3H, t), 0.98 (6H, t) ppm.

PREPARATION EXAMPLE 7

Method of Preparing Heptabenzyl Ester of S2 Compound

To a solution of S2 anhydride (50 mg) in tetrahydrofuran (2 mL) were added p-bromobenzyl alcohol (51 mg) and 2-(p-bromobenzyl)-1,3-diisopropylisourea (140 mg), and the mixture was allowed to undergo a reaction at room temperature for three days. In the course of the reaction, p-bromobenzyl alcohol (51 mg) and 2-(p-bromobenzyl)-1,3-diisopropylisourea (140 mg) were added four times. To this reaction mixture was admixed hexane and the resultant was filtered, followed by removal of the solvent under reduced pressure. A resulting crude product was purified with a silica gel column chromatography and eluted with a mixture of hexane and ethyl acetate [4:1 (v/v)]. The solvent of the eluted fraction containing the desired product was removed under reduced pressure to afford heptabenzyl ester of S2 compound (68 mg). The $^1$H-NMR and IR data of this compound were as shown below. From these data, the compound thus obtained was confirmed to be a derivative in which all the carboxyl groups of S2 compound were benzylated.

a) $^1$H-NMR (D$_2$O): δ (integrated value, multiplicity): 7.38–7.52 (14H, m), 7.02–7.18 (14H, m), 6.26 (1H, dt), 5.86 (1H, dt), 4.70–5.05 (14H, m), 2.04–2.70 (14H, m), 1.15–1.60 (6H, m), 0.94 (3H, t), 0.70–0.82 (6H, m) ppm.

b) Infrared absorption spectrum (neat, NaCl plate): $v_{max}$: 2965, 1733, 1713 cm$^{-1}$.

PREPARATION EXAMPLE 8

Method of Preparing t-Butyl Hexamethyl Ester of S2 Compound

To a solution of S2 anhydride (100 mg) in methyilene chloride (2 mL) were added cyclohexane (2 mL), t-butanol (0.5 mL), t-butyl-2,2,2-trichloroacetimidate (79 mg) and boron trifluoride ether complex (0.05 mL), and the mixture liquid was allowed to undergo a reaction at room temperature for 15 hours. To this reaction mixture was added water, and the resultant was extracted with ethyl acetate. Thereafter, a resulting organic layer was washed with a citric acid aqueous solution and a saline solution, and dried over magnesium sulfate. The residue obtained by removing the solvent under reduced pressure was dissolved in ether (2 mL) and methanol (2 mL), then admixed with a solution of trimethylsilyldiazomethane in hexane (2M, 0.5 mL), and allowed to undergo a reaction at room temperature for four days. A crude product obtained by adding acetic acid to the reaction mixture and removing the solvent under reduced pressure was purified with a silica gel column chromatography and eluted with a mixture of hexane and ethyl acetate [5:2 (v/v)]. The solvent of the eluted fraction containing the desired product was removed under reduced pressure to afford t-butyl hexamethyl ester of S2 compound (106 mg). The $^1$H-NMR data of this compound were as shown below. From these data, the compound thus obtained was confirmed to be a derivative in which the carboxyl groups bonded to the saturated carbon atoms in the structural formula of S2 compound were t-butylated, while all the other carboxyl groups were methylated.

$^1$H-NMR (D$_2$O): δ (integrated value, multiplicity): 6.00 (1H, dt), 3.84 (3H, s), 3.75 (3H, s), 3.72 (9H, s), 3.71 (3H, s), 2.64 (2H, t), 2.16–2.41 (12H, m), 1.44 (9H, s), 1.22–1.60 (6H, m), 1.05 (3H, t), 0.83–0.94 (6H, m) ppm.

PREPARATION EXAMPLE 9

Method of Preparing Hexamethyl Ester of S2 Compound

To a solution of the above t-butyl hexamethyl ester of S2 compound (100 mg) in m ethylene chloride (2 mL) was added trifluoroacetic acid (2 mL) and the mixture was allowed to undergo a reaction at room temperature for 1.5 hours. After removal of the solvent under reduced pressure, the reaction mixture was subjected to azeotropy twice with toluene to afford hexamethyl ester of S2 compound (95 mg). The $^1$H-NMR data of this compound were as shown below. From these data, the compound thus obtained was confirmed to be a derivative in which all the carboxyl groups except for the carboxyl groups bonded to the saturated carbon atoms in the structural for mula of S2 compound were methylated.

$^1$H-NMR (D$_2$O): δ (integrated value, multiplicity): 6.30 (1H, dt), 6.02 (1H, dt), 3.85 (3H, s), 3.69–3.75 (15H, m), 2.19–2.70 (14H, m), 1.20–1.65 (6H, m), 1.04 (3H, t), 0.83–0.94 (6H, m) ppm.

PREPARATION EXAMPLE 10

Method of Preparing p-bromophenacyl Hexamethyl Ester of S2 Compound

To a solution of the above hexamethyl ester of S2 compound (95 mg) in ethyl acetate (2 mL) were added triethylamine (20 mg) and p-bromophenacyl bromide (34 mg), followed by stirring at room temperature. After lapse of two hours, triethylamine (20 mg) and p-bromophenacyl bromide (34 mg) were further added and the mixture liquid was allowed to undergo a reaction for 2 hours. After the reaction, the reaction mixture was extracted into an organic layer by adding ethyl acetate and water thereto, washed with a saline solution, and dried over magnesium sulfate. A crude product obtained by removing the solvent under reduced pressure was purified with a silica gel column chromatography and eluted with a mixture of hexane and ethyl acetate [3:2 (v/v)]. The solvent of the eluted fraction containing the desired product was removed under reduced pressure to afford p-bromophenacyl hexamethyl ester of S2 compound (100 mg). The $^1$H-NMR, IR and mass spectrometric analysis data of this compound were as shown below. From these data, the compound thus obtaned was confirmed to be a derivative in which the carboxyl groups bonded to the saturated carbon atoms in the structural formula of S2 compound were pbromophenacylated, while all the other carboxyl groups were methylated.

a) $^1$H-NMR (D$_2$O): δ (integrated value, multiplicity): 7.78 (2H, d), 7.64 (2H, d), 6.31 (1H, dt), 5.97 (1H, dt), 5.30 (2H, s), 3.83 (3H, s), 3.76 (3H, s), 3.74 (3H, s), 3.72 (3H, s), 3.70 (6H, s), 2.18–2.80 (14H, m), 1.20–1.65 (6H, m), 1.03 (31H, t), 0.88 (6H, t) ppm.

b) Infrared absorption spectrum (neat, NaCl plate): $v_{max}$: 2955, 1747, 1726, 1427 cm$^{-1}$.

c) Mass spectrum (MALDI): 913 [M+Na]$^+$, 915 [M+2+Na]$^+$.

PREPARATION EXAMPLE 11

Synthetic Preparation of S0 Anhydride

S0 anhydride was prepared in the following manner. First, from known compounds, ethyl diethylphosphonobromoacetate and dimethyl 2-ketoglutarate, was synthesized the following S0 intermediate product 1:

S0 INTERMEDIATE PRODUCT 1

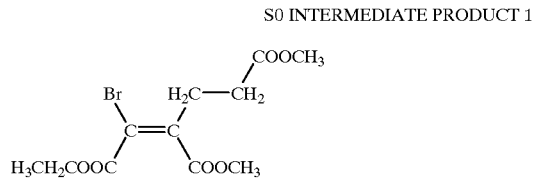

and this S0 intermediate product 1 was allowed to react with butenyldisiamylborane to synthesize the following S0 intermediate product 2:

S0 INTERMEDIATE PRODUCT 2

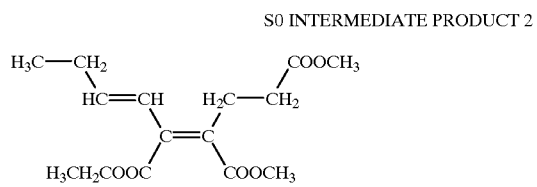

Finally, this S0 intermediate product 2 was hydrolyzed under an alkaline condition to give a sodium salt, which was then treated under an acidic condition to afford S0 anhydride.

Each step of these processes is described in detail below.

For the first process, lithium chloride (4.7 g) was added to a solution of ethyl diethylphosphonobromoacetate (48 g) in acetonitrile (400 mL) under ice-cooling, and diisopropylamine (14.3 g) was added dropwise. After stirring the mixture as it is for one hour, dimethyl 2-ketoglutarate (13.7 g) was added dropwise to the mixture, and the resultant was allowed to undergo a reaction under ice-cooling. After the reaction was completed, the solvent was removed under reduced pressure and the resultant was admixed with ethyl acetate, washed with water, and dried over magnesium sulfate. A crude product obtained by removing the solvent under reduced pressure ws purified with a gilica gel column chromatography and eluted with a mixture of hexanke and ethyl acetate [4:1 (v/v)]. The solvent of the eluted fraction containing the desired product was removed under reduced pressure to afford S0 intermediate product 1 (19.5 g). The $^1$H-NMR data of this compound were as shown below.

$^1$H-NMR (D$_2$O): δ (integrated value, multiplicity): 4.25 (2H, q), 3.79 (3H, s), 3.70 (3H, s), 2.87 (2H, t), 2.53 (2H, t), 1.33 (3H, t).

Subsequently, to a solution of the above S0 intermediate product 1 (46.1 g) in dioxane (1.5 L) were added a solution of butenyldisiamylborane in tetrahydrofuran (0.47 mol/L, 500 mL), potassium carbonate (74.1 g), potassium phosphate (56.9 g)and tetrakistriphenylphosphine palladium (3.1 g) under a nitrogen atmosphere, and the resulting mixture was heated to 100° C. under stirring. After lapse of 2 hours 40 minutes, tetrakistriphenylphosphine palladium (0.5 g) and potassium carbonate (5.0 g) were added to the mixture, and the resultant was allowed to undergo a reaction for further 12 hours. After the reaction, a crude product obtained by removing the solvent under reduced pressure was purified with a silica gel column chromatography and eluted with a mixture of hexane and ethyl acetate [5:1 (v/v)]. The solvent of the eluted fraction containing the desired product was removed under reduced pressure to afford S0 intermediate product 2 (31.6 g). The $^1$H-NMR data of this compound were as shown below.

$^1$H-NMR (D$_2$O): δ (integrated value, multiplicity): 6.38 (1H, dt), 6.06 (1H, dt), 4.33 (2H, q), 3.75 (3H, s), 3.69 (3H, s), 2.71–2.81 (2H, m), 2.44–2.54 (2H, m), 2.17–2.28 (2H, m), 1.35 (3H, t), 1.06 (3H, t).

Subsequently, the above S0 intermediate product 2 (32.0 g) was dissolved in dioxane (250 mL) and water (150 mL), then the solution was admixed with a sodium hydroxide aqueous solution (400 g/L, 53.5 mL) and allowed to undergo a reaction at room temperature for 14 hours. After the reaction was completed, the solvent was removed under reduced pressure and water and duisopropyl ether were added to the resultant to extract a crude product into an aqueous layer. The aqueous layer was adjusted to pH 3 by addition of a citric acid aqueous solution, allowed to stand for one hour, and thereafter extracted with ethyl acetate and dried over magnesium sulfate. A crude product obtained by removing the solvent under reduced pressure was purified with a silica gel column chromatography and eluted with a mixture of hexane, ethyl acetate and acetic acid [2:1:0.1 (v/v/v)]. The solvent of the eluted fraction containing the desired product was removed under reduced pressure to afford crude S0 compound (13.6 g). After recrystallization from ether-hexane, further recrystallization from ethyl acetate-hexane was performed to afford S0 anhydride (7.7 g). The $^1$H-NMR data of this compound agreed to the values of S0 anhydride shown in preparation example 1 and those described in the literature references.

PREPARATION EXAMPLE 12

Method of Preparing a Derivative of R0 Compound from the Filtrate

To a solution of the oily substance (1.13 g) obtained from the filtrate in preparation example 1 in methylene chloride (15 mL) was added p-bromoaniline (1.5 g), followed by stirring at room temperature for 8 hours, and diisopropylcarbodimide (1.1 g) was added and the resulting mixture was allowed to unldergo a reaction for one hour. The solvent of the reaction liquid was removed under reduced pressure, and the resultant was extracted by addition of ethyl acetate and 0.5N hydrochloric acid, washed with water, and dried over sodium sulfate. A crude product obtained by removing the solvent under reduced pressure was purified with a silica gel column chromatography and eluted with a mixture of hexane and ethyl acetate [9:1 (v/v)]. The solvent of the eluted fraction containing the desired product was removed under reduced pressure to afford a derivative of R0 compound (40 mg). The $^1$H-NMR, IR and elemental analysis data of this compound were as shown below. From these data, the above derivative was confirmed to be a derivative in which the carboxyl groups bonded to the saturated carbon atoms in the structural formula of R0 compound were p-bromoanilidated, while other carboxyl groups were (p-bromophenyl) imidated.

As can also be found from the results, R0 compound was produced in the culture filtrate.

a) $^1$H-NMR (D$_2$O): δ (integrated value, multiplicity): 7.60 (2H, d), 7.41 (4H, s), 7.34 (1H, d), 7.29 (1H, s), 7.26 (2H, d), 6.46 (1H, d), 3.62 (2H, s), 2.35 (2H, q), 1.13 (3H, t) ppm.

b) Infrared absorption spectrum (nujol, NaCl plate): $v_{max}$: 3345, 1708, 1685, 1640, 1589 cm$^{-1}$.

c) Elemental analysis (C$_{22}$H$_{18}$N$_2$O$_3$Br).

|  | C | H | N |
|---|---|---|---|
| calculated: | 50.99 | 3.50 | 5.40 |
| found: | 50.30 | 3.41 | 5.31 |

PREPARATION EXAMPLE 13

Method of Preparing Botylamide Tetrasodium Salt of S1 Compound

Diphenyiphosphoryl acid chloride (577 mg) and N-methyl morphorine (430 mg) were added to a solution of S1 anhydride (840 mg) in acetonitrile (8 mL) under ice-cooling, followed by stirring for one hour. To the solution were further added n-butylamine (157 mg ) under ice-cooling, and the resultant was allowed to undergo a reaction for one hour. After the reaction was completed, the reaction mixture was admixed with ethyl acetate, washed with a citric acid aqueous solution, and dried over magnesium sulfate. A crude product obtained by removing the solvent under reduced pressure was purified with a silica gel column chromatography and eluted with a mixture of hexane and ethyl acetate [1:1 (v/v)]. The solvent of the eluted fraction containing the desired product was removed under reduced pressure to afford butylamide of S1 anhydride (190 mg). The $^1$H-NMR and IR data of this compound were as shown below. From these data, the compound thus obtained was confirmed to be a derivative in which a carboxyl group of S1 anhydride was butylamidated.

a) $^1$H-NMR (D$_2$O): δ (integrated value, multiplicity): 7.30 (1H, dt), 6.22 (1H, d), 5.45–5.60 (1H, m), 3.12–3.25 (2H, m), 2.80 (2H, t), 2.10–2.65 (9H, m), 1.20–1.50 (6H, m), 1.12 (3H, t), 0.87–1.02 (6H, m) ppm.

b) Infrared absorption spectrum (neat, NaCl plate): $v_{max}$: 2970, 1818, 1769, 1648 cm$^{-1}$.

Subsequently, to the above butylamide of S1 anhydride (160 mg) were added a sodium bicarbonate aqueous solution (NaHCOs 121 mg, water 20 mL) and 1,4-dioxane (20 mL), and the resultant was allowed to undergo a reaction at room temperature for 16 hours. After the reaction was completed, the solvent was removed under reduced pressure to afford butylamide tetrasodium salt of S1 compound (200 mg). The $^1$H-NMR and IR data of this compound were as shown below. From these data, the compound thus obtained was confirmed to be a derivative in which the carboxyl groups bonded to the saturated carbon atoms in the structural formula of S1 compound were butylamidated, while other carboxyl groups were substituted with sodium salt.

a) $^1$H-NMR (D$_2$O): δ (integrated value, multiplicity): 6.36 (1H, d), 5.88 (1H, dt), 2.10–2.65 (10H, m), 1.25–1.60 (7H, m), 1.01 (3H, t), 0.80–0.95 (6H, m) ppm.

b) Infrared absorption spectrum (KBr): ν$_{max}$: 3425, 1635, 1550, 1398 cm$^{-1}$.

PREPARATION EXAMPLE 14

Method of Preparing t-Butyl Ester Tetrasodium Salt of S1 Compound

To a solution of S1 anhydride (500 mg) in methylene chloride (4 mL) were added cyclohexane (4 mL), t-butyl-2,2,2-trichloroacetimidate (308 mg), and boron trifluoride ether complex (0.05 mL), and the mixture liquid was allowed to undergo a reaction at room temperature for 4 hours. After the reaction, the reaction mixture was admixed with hexane and filtered, and the solvent was removed under reduced pressure to give a crude product, which in turn was purified with a silica gel column chromatography and eluted with a mixture of hexane and ethyl acetate [1:1 (v/v)]. The solvent of the eluted fraction containing the desired product was removed under reduced pressure to afford. t-butyl ester of S1 compound (240 mg). The $^1$H-NMR and IR data of this compound were as shown below. From these data, the compound thus obtained was confirmed to be a derivative in which a carboxyl group of S1 anhydride was tbutylated.

a) $^1$H-NMR (D$_2$O): δ (integrated value, multiplicity): 7.30 (1H, dt), 6.21 (1H, dt), 2.11–2.75 (11H, m), 1.41 (9H, s), 1.22–1.55 (2H, m), 1.08 (3H, t), 0.99 (3H, t) ppm.

b) Infrared absorption spectrum (neat, NaCl plate): ν$_{max}$: 2975, 1820, 1771, 1722 cm$^{-1}$.

Subsequently, to the above t-butyl ester of S1 anhydride (218 mg) were added a sodium bicarbonate aqueous solution (NaHCO$_3$ 164 mg, water 20 mL) and 1,4-dioxane (20 mL), and the resultant was allowed to undergo a reaction at room temperature for 20 hours. After the reaction was completed, the solvent was removed under reduced pressure to afford t-butyl ester tetrasodium salt of S1 compound (276 mg). The $^1$H-NMR and IR data of this compound were as shown below. From these data, the compound thus obtained was confirmed to be a derivative in which the carboxyl groups bonded to the saturated carbon atoms in the structural formula of S1 compound were t-butylated, while other carboxyl groups were substituted with sodium salt.

a) $^1$H-NMR (D$_2$O): δ (integrated value, multiplicity): 6.36 (1H, d), 5.87 (1H, dt), 2.10–2.60 (10H, m), 1.47 (9H, s), 1.20–1.65 (3H, m), 1.01 (3H, t), 0.86 (3H, t) ppm.

b) Infrared absorption spectrum (KBr): ν$_{max}$: 3405, 1705, 1551, 1403 cm$^{-1}$.

PREPARATION EXAMPLE 15

Method of Preparing Benzylamide Tetrasodium Salt of S1 Compound

Diphenylphosphoryl acid chloride (344 mg) and N-methyl morpholine (260 mg) were added to a solution of S1 anhydride (500 mg) in acetonitrile (5 mL) under ice-cooling, an the resulting solution was allowed to undergo a reaction for one hour and, after addition of benzylamine (137 mg), further allowed to undergo a reaction for one more hour. After the reaction was completed, a crude product obtained by removing the solvent under reduced pressure was purified with a silica gel column chromatography and eluted with a mixture of hexane and ethyl acetate [1:1 (v/v)]. The solvent of the eluted fraction containing the desired product was removed under reduced pressure to afford benzylamide of S1 anhydride (159 mg). The $^1$H-NMR and IR data of this compound were as shown below. From these data, the compound thus obtained was confirmed to be a derivative in which a carboxyl group of S1 anhydride was benzylamidated.

a) $^1$H-NMR (D$_2$O): δ (integrated value, multiplicity): 7.15–7.38 (6H, m), 6.21 (1H, d), 5.70–5.82 (1H, m), 4.38 (2H, d), 2.83 (2H, t), 2.10–2.63 (9H, m), 1.20–1.42 (2H, m), 1.11 (3H, t), 0.99 (3H, t) ppm.

b) Infrared absorption spectrum (neat, NaCl plate): ν$_{max}$: 1820, 1750, 1640 cm$^{-1}$.

Subsequently, to the above benzylamide of S1 anhydride (157 mg) were added a sodium bicarbonate aqueous solution (NaHCO$_3$ 110 mg, water 20 mL) and 1,4-dioxane (20 mL), and the resultant was allowed to undergo a reaction at room temperature for 16 hours. After the reaction was completed, the solvent was removed under reduced pressure to afford benzylamide tetrasodium salt of S1 compound (196 mg). The $^1$H-NMR and IR data of this compound were as shown below. From these data, the compound thus obtained was confirmed to be a derivative in which the carboxyl groups bonded t the saturated carbon atoms in the structural formula S1 compound were benzylamidated) while other carboxyl groups were substituted with sodium salt.

a) $^1$H-NMR (D$_2$O): δ (integrated value, multiplicity): 7.25–7.50 (5H, m), 6.35 (1H, d), 5.85 (1H, dt), 4.40 (2H, s), 2.10–2.70 (10H, m), 1.20–1.65 (3H, m), 0.99 (3H, t), 0.85 (3H, t) ppm.

b) Infrared absorption spectrum (KBr): ν$_{max}$: 3405, 1641, 1555, 1403 cm$^{-1}$.

PREPARATION EXAMPLE 16

Method of Preparing Diimide of S1 Compound

Ammonia water (0.5 mL) and acetic acid (0.1 mg) were added to a solution of S1 anhydride (0.3 g) in 1,4-dioxae (5 mL) in a stream of argon, and the resulting solution was allowed to undergo a reaction at 105° C. for nine hours. After the reaction was completed, a crude product obtained by removing the solvent under reduced pressure was purified with a silica gel column chromatography and eluted with a mixture of hexane, chloroform and methanol [2:7:1 (v/v/v)]. The solvent of the eluted fraction containing the desired product was removed under reduced pressure to afford diimide of S1 compound (0.2 g). The $^1$H-NMR and IR data of this compound were as shown below. From these data, the compound thus obtained was confirmed to be a derivative in which the two carboxyl groups bonded to adjacent carbon atoms in S1 compound were imidated.

a) $^1$H-NMR (D$_2$O): δ (integrated value, multiplicity): 8.53 (1H, s), 8.41 (1H, s), 7.09 (1H, dt), 6.15 (1H, dt), 2.68 (4H, s), 2.36–2.48 (2H, m), 2.19–2.34 (4H, m), 2.05–2.18 (1H, m), 1.28–1.36 (2H, m), 1.06 (3H, t), 0.94 (3H, t) ppm.

b) Infrared absorption spectrum (neat, NaCl plate): ν$_{max}$: 2500–3500, 1731, 1714, 1682, 1349, 1070 cm$^{-1}$.

PREPARATION EXAMPLE 17

Method of Preparing Bis(p-bromophenyl)imide of S1 Compound

To a solution of S1 anhydride (0.3 g) in 1,4-dioxanle (5 mL) were added p-bromoaniline (0.4 mL) and acetic acid (0.1 mL) in a stream of argon, and the resulting solution was allowed to undergo a reaction at 105° C. for nine hours. After the reaction was completed, a crude product obtained by removing the solvent under reduced pressure was purified with a silica gel column chromatography and eluted with a mixture of hexane, chloroform and methanol [6:7:1 (v/v/v)]. The solvent of the eluted fraction containing the desired product was removed under reduced pressure to afford bis(p-bromophenyl)imide of S1 compound (0.3 g). The $^1$H-NMR and IR data of this compound were as shown below. From these data, the compound thus obtained was confirmed to be a derivative in which the two carboxyl groups bonded to adjacent carbon atoms S1 compound were (p-bromophenyl)imidated.

a) $^1$H-NMR ($D_2O$): δ (integrated value, multiplicity): 7.50–7.56 (4H, m), 7.15–7.24 (5H, m), 6.24 (1H, dt), 2.70–2.80 (4H, m), 2.54–2.62 (2H, m), 2.40–2.47 (2H, m), 2.24–2.30 (3H, m), 1.35–1.48 (2H, m), 1.08 (3H, t), 1.03 (3H, t) ppm.

b) Infrared absorption spectrum (neat, NaCl plate): $v_{max}$: 2500–3500, 1738, 1713, 1681, 1493, 1392, 1242, 1120 $cm^{-1}$.

In the following examples 1 to 4, the dispersing activity of each dispersant of the present invention in a dilute solution was evaluated using the turbidity or a like characteristic of the liquid as an indication.

EXAMPLE 1

Evaluation of Dispersine Activity in a Dilute Solution (with respect to kaolin)

First, 10% kaolin suspension was prepared by adding distilled water (300 mL) to kaolin (30 g: WAKO PURE CHEMICAL INDUSTRIES) and applying ultrasonic wave to the resultant (for 15 minutes at the maximum output) with use of an ultrasonic cleaner ("UT0205" manufactured by SHARP).

Subsequently, the kaolin suspension (10 mL) and each of the test sample aqueous solutions (1 mL each) shown in Table 7 were pipetted into a test tube, stirred for 15 seconds with a point mixer, and thereafter allowed to stand on a vibration-free plate for 24 hours. It is to be noted that each test sample was added in amounts of 0.1% and 0.5% (solids content weight ratio) relative to the dispersoid particles (kaolin). After the standing, the sedimentation volume of kaolin particles was measured, the results of which are shown also in Table 7. The sedimentation volume serves as an indication of dispersibility, and a smaller sedimentation volume indicates more excellent dispersibility.

TABLE 7

| | Sedimentation volume | | | |
|---|---|---|---|---|
| Test sample | 0.02% added | 0.1% added | 0.5% added | 2.0% added |
| Addition of filtrate | 3.2 | 3.2 | 2.3 | 1.5 |
| Addition of pentasodium salt of S1 compound | 3.1 | 1.2 | 1.0 | 1.0 |
| Addition of heptasodium salt of S2 compound | 3.1 | 1.1 | 1.0 | 1.1 |
| Addition of lignin sulfonate | 3.2 | 2.7 | 1.2 | 1.2 |
| No addition (control) | | 3.3 | | |

As seen from Table 7, any of the cases respectively using the filtrate, pentasodium salt of S1 compound and heptasodium salt of S2 compound as test samples exhibited better dispersibility than the controls (no addition group). Further, the pentasodiumn salt of S1 compound and the heptasodium salt of S2 compound each exhibited a higher activity than the existing dispersant, i.e., lignin sulfonate, and demonstrated a sufficient activity when 0.1% added On the other hand, the filtrate sample exhibited as high an activity as lignin sulfonate.

EXAMPLE 2

Evaluation of Dispersing Activity in a Dilute Solution (with respect to calcium carbonate)

The same procedure as in example 1 except for the use of calcium carbonate instead of kaolin as dispersoid was performed to measure the sedimentation volume of each of the test samples shown in Table 8. Note that calcium carbonate was applied with ultrasonic wave (for 15 minutes at the maximum output) with use of an ultrasonic cleaner ("UT205" manufactured by SHARP) as was kaolin to prepare 10% calium carbonate suspension (30 g/300 mL). The results obtained are shown also in Table 8. The sedimentation volume serves as an indication of dispersibility, and a smaller sedimentation volume indicates more excellent dispersibility.

TABLE 8

| | Sedimentation volume | |
|---|---|---|
| Test sample | 0.1% added | 0.5% added |
| Addition of filtrate | 3.73 | 2.59 |
| Addition of pentasodium salt of S1 compound | 3.63 | 3.04 |
| Addition of heptasodium salt of S2 compound | 3.45 | 2.90 |
| No addition (control) | 5.66 | |

As seen from Table 8, any of the cases respectively using the filtrate, pentasodium salt of S1 compound and heptasodium salt of S2 compound as test samples exhibited much better dispersibility than the controls (no addition group). Further, in any case, the 0.5% added group exhibited a higher degree of dispersibility than the 0.1% added group.

EXAMPLE 3

Evaluation of Dispersing Activity in a Dilute Solution (with respect to cement)

Into a test tube were pipetted each of test samples having predetermined concentrations (1 mL each) shown in Table 9 and a suspension (4 mL: 31.3 g/500 mL) of cement (produced by CHICHIBUONODA CEMENT), and the resultant was stirred with a point mixer and thereafter allowed to stand stationary, followed by visual observation as to its dispersion state with lapse of time. A case where a dispersion state was retained for more than two hours was judged "◯" which was meant to exhibit a dispersing effect, while other cases were each judged "X" which was meant not to exhibit the dispersing effect. The results of the judgment are shown also in Table 9.

TABLE 9

| Test sample | Concentration (mg/ml) | | | | | | | | |
|---|---|---|---|---|---|---|---|---|---|
| | 0 | 0.5 | 1.0 | 2.0 | 3.0 | 4.0 | 5.0 | 7.5 | 10.0 | 14.5 |
| Addition of filtrate | X | X | X | X | ○ | ○ | ○ | ○ | ○ | ○ |
| Addition of pentasodium salt of S1 compound | X | X | X | X | X | X | X | ○ | ○ | ○ |
| Addition of heptasodium salt of S2 compound | X | X | X | ○ | ○ | ○ | ○ | ○ | ○ | ○ |

Note:
"○": dispersing effect resulted;
"X": dispersing effect not resulted.

As seen from Table 9, a desired dispersing effect resulted in the filtrate-added group at a concentration of 3.0 mg/mL or more, in the group added with pentasodium salt of S1 compound at a concentration of 7.5 mg/mL or more, and in the group added with heptasodium salt of S2 compound at a concentration of 2.0 mg/mL or more.

EXAMPLE 4

Evaluation of Dispersing Activity in a Dilute Solution (with respect to carbon black)

First, a carbon black suspension was prepared by adding carbon black (80 mg) to water (1 L) and applying ultrasonic wave to the resultant (for 15 minutes at the maximum output) with use of an ultrasonic cleaner ("UT0205" manufactured by SHARP).

Subsequently, the carbon black suspension (10 mL) thus obtained was pipetted into a test tube, to which is then added each test sample in a predetermined amount, and the resultant was stirred for 15 seconds with a point mixer and thereafter allowed to stand on a vibration-free plate for five hours. After the standing, the resultant was admixed with 3% sodium chloride aqueous solution (1 mL), stirred for 15 seconds with a point mixer, and again allowed to stand on the vibration-free plate for 19 hours. Thereafter, a supernatant liquid (about 2 cm from the upper surface) in the test tube was collecte and measured for absorbance (wavelength: 660 nm).

Evaluation of dispersibility was made in the following manner. First, the relationship between the carbon black concentration and the absorbance was found in advance, and from the absorbance measured the concentration of carbon black suspended in the test tube was calculated. With the flotation rate of the first-prepared carbon black suspension assumed 100%, the flotation rate of particles suspended was found from the carbon black concentration calculated based on the absorbance. The results are shown in Table 10.

TABLE 10

| Amount of filtrate added (solids content) (mg/L) | 0 | 13 | 26 | 40 | 53 | 66 |
|---|---|---|---|---|---|---|
| Flotation rate of carbon black | 3.1 | 2.9 | 10.3 | 67.8 | 79.1 | 83.8 |

The carbon black suspension used in the test was a highly stable suspension since the carbon black used was as fine as 20 nm in average particle diameter. The dispersibility was evaluated by adding an electrolyte (sodium chloride) in order to cause the suspension to agglomerate forcibly.

From Table 10, the filtrate (freeze-dried) was found to exhibit a dispersing activity of 40 mg/L or more under the conditions under which carbon black with no addition did not float (or agglomerated and sedimented).

In the following examples 5 to 9, the dispersing ability in concentrated solutions was evaluated using the viscosity or a like characteristic of each liquid as an indication thereof.

EXAMPLE 5

Evaluation of Dispersing Activity in a Concentrated Solution (with respect to kaolin . . . case 1)

At a room temperature of 25° C., kaolin (42 g) and distilled water (60 g) containing the filtrate obtained in culture example 1 were placed in a vessel, followed by stirring for one minute with a hand mixer. Subsequently, the mixture liquid was mixed sufficiently intimate with a spoon stirring at the bottom and inner periphery of the vessel, and further stirred for two minutes with the hand mixer. Immediately thereafter, the mixture liquid was measured for viscosity using a Brookfield rotational viscometer (number of revolutions: 60 rpm, rotor used: No. 3). The results of measurement are shown in Table 11.

TABLE 11

| Test sample (solid content wt %/kaolin) | Viscosity (mPa · s) |
|---|---|
| Distilled water only | 700 |
| 0.1 | 340 |

As seen from Table 11, the case with use of the filtrate of culture example 1 exhibited a considerably lowered viscosity as compared with the case without use of the filtrate and hence good dispersibility.

EXAMPLE 6

Evaluation of Dispersing Activity in a Concentrae Solution (with respect to kaolin . . . case 2)

At a room temperature of 25° C., each of the sample solutions shown in Table 11 (3 mL each) and kaolin (2 g) were placed in a vessel. This specimen was stirred for one minute with a point mixer, treated with ultrasonic wave for three minutes, and thereafter measured for viscosity with an E-type viscometer (measurable viscosity range: 93–932 mPa·s). The results of measurement are shown in Table 12.

TABLE 12

| Sample solutions | | Viscosity (mPa · s) |
|---|---|---|
| No addition (distilled water only) | | 384 ± 8.6 |
| Pentasodium salt of S1 compound | 0.020% (w/v) | 314 ± 14.4 |
| | 0.033% (w/v) | 239 ± 19.2 |
| | 0.047% (w/v) | 134 ± 22.7 |
| Heptasodium salt of S2 compound | 0.020% (w/v) | 340 ± 22.2 |
| | 0.033% (w/v) | 233 ± 15.5 |
| | 0.047% (w/v) | 89 ± 8.9 |
| Filtrate (freeze-dried) | 0.033% (w/v) | 347 ± 24.9 |
| | 0.067% (w/v) | 281 ± 28.7 |
| | 0.135% (w/v) | 122 ± 4.1 |

As seen from Table 12, a marked viscosity decrease in a concentration-dependent fashion, which indicated good dispersibility, was observed in any of the cases respectively using the pentasodium salt of S1 compound, heptasodium salt of S2 compound and filtrate containing these compounds.

EXAMPLE 7

Evaluation of Dispersing Activity in a Concentrated Solution (with respect to barium sulfate)

The same procedure as in example 5 except for the use of barium sulfate (42 g) instead of kaolin was performed to measure the viscosity of each test sample. The results of measurement are shown in Table 13.

TABLE 13

| Amount added (solids content | Viscosity (mPa · s) | |
|---|---|---|
| wt %/barium sulfate) | Filtrate | Lignin sulfonate |
| Distilled water only | | 700 |
| 0.1 | 480 | 440 |
| 0.3 | 20 | 285 |
| 0.5 | 60 | 120 |

As seen from Table 13, the case with use of the filtrate of culture example 1 exhibited a remarkable decrease in viscosity as compared with the case without use of the filtrate or with use of lignin sulfonate and hence demonstrated good dispersibility.

EXAMPLE 8

Evaluation of Dispersing Activity in a Concentrated Solution (with respect to calcium carbonate)

The same procedure as in example 5 except for the use of calcium carbonate (40 g) instead of kaolin was performed to measure the viscosity of each test sample. The results of measurement are shown in Table 14.

TABLE 14

| Amount added (solids content | Viscosity (mPa · s) | |
|---|---|---|
| wt %/calcium carbonate) | Filtrate | Lignin sulfonate |
| Distilled water only | | 680 |
| 0.1 | 250 | 200 |
| 0.3 | 250 | 160 |
| 0.9 | 230 | 160 |
| 3.0 | 240 | 230 |

As seen from Table 14, the case with use of the filtrate of culture example 1 exhibited a remarkable decrease in viscosity as compared with the case without use of the filtrate and hence demonstrated superior dispersibility. Further, the degree of dispersibility of the case using the filtrate was substantialy as high as that of the case using lignin sulfonate.

EXAMPLE 9

Evaluation of Dispersing Activity in a Concentrated Solution (with respect to light calcium carbonate)

The same procedure as in example 5 except for the use of light calcium carbonate (40 g) instead of kaolin was performed to measure the viscosity of each test sample. The results of measurement are shown in Table 15.

TABLE 15

| Amount added (solids content | Viscosity (mPa · s) | |
|---|---|---|
| wt %/light calcium carbonate) | Filtrate | Lignin sulfonate |
| Distilled water only | | 790 |
| 0.3 | 245 | 220 |
| 0.9 | 183 | 100 |

As seen from Table 15, the case with use of the filtrate of culture example 1 exhibited a remarkable decrease in viscosity as compared with the case without use of the filtrate and hence demonstrated good dispersibility. Further, the degree of dispersibility of the case using the filtrate was substantially as high as that of the case using lignin sulfonate.

EXAMPLE 10

Evaluation of Dispersing Activity in a Concentrated Solution (with respect to feldspar glaze)

The same procedure as in example 5 except for the use of feldspar glaze (50 g) instead of kaolin was performed to measure the viscosity of each test sample. In this example, the viscosity of each sample was measured after lapse of one month and two months from stirring as well as immediately after stirring. The results of measurement are shown in Table 16.

TABLE 16

| Amount added | Viscosity (mPa · s) | | |
|---|---|---|---|
| (solids content wt %/feldspar glaze) | Immediately after stirring | one month after stirring | two months after stirring |
| Distilled water only | 720 | 800 | 800 |
| 0.15 | 620 | 680 | 610 |
| 0.45 | 480 | 300 | 320 |

As seen from Table 16, the case with use of the filtrate of culture example I exhibited a remarkable decrease in viscosity as compared with the case without use of the filtrate and hence demonstrated good dispersibility. Further, the dispersibility tended to improve as the duration of storage months increased in the case where the solids content of the filtrate was added in an amount of 0.45 wt % relative to feldspar glaze.

EXAMPLE 11

Evaluation of Dispersing Activity by a Mortar Test

The water-reducing performance of a mortar admixed with the filtrate obtained in culture example 1 was examined by comparison with that of a mortar admixed with commercially available lignin sulfonate.

(1) Materials used and blending of mortar

This example used, per batch, materials including common Portland cement (600 g, specific gravity: 3.16) specified by JIS R5210, river sand (1800 g, specific gravity: 2.67, coarse grain rate: 2.99), and water or an aqueous solution (310 g) containing the filtrate obtained in culture example 1.

In practice, an anti-foaming agent was added to the blend to adjust the amount of entrained air to about 2%.

(2) kneading and mixing of mortar

The mortar was kneaded and mixed according to JIS R5201, and the mortar (about 1.2 L) per batch was kneaded and mixed for three minutes with a mortar mixer.

(3) Measurement of slump

The slump of the mortar was measured according to JIS A1173 by means of a slump cone (internal diameter at top: 50 mm, internal diameter at bottom: 100 mm, and height: 150 mm). Measurement was performed at two points: immediately after the kneading and mixing, and after lapse of 60 minutes from the kneading and mixing. The measurement of slump after lapse of 60 minutes was performed as follows: the mortar having been measured for slump immediately after the kneading and mixing was put back into the mixing vessel, allowed to stand therein for 60 minutes, and then kneadingly turned over about 10 times with a kneading spoon. The results of measurement are shown in Table 17. It should be noted that the greater the measured slump value, the more excellent the dispersibility.

TABLE 17

| Test sample | Added amount of solids content %/C | Slump (cm) immediately after | Slump (cm) after lapse of 60 minutes |
| --- | --- | --- | --- |
| No addition (control) | 0 | 4.7 | — |
| Lignin sulfonate | 0.25 | 8.7 | 5.8 |
| Filtrate | 0.25 | 9.7 | 8.1 |
| Filtrate | 0.15 | 9.0 | 7.2 |

As seen from Table 17, the case with use of the filtrate obtained in culture example 1 exhibited a remarkable improvement in slump as compared with the case without use of the filtrate. As to the degree of dispersibility, the case with use of the filtrate was better than the case with use of lignin sulfonate, and the difference in dispersibility between the two became more conspicuous after lapse of 60 minutes advantageously.

EXAMPLE 12

Evaluation of Dispersing Activity with Respect to an Organic Pigment in an Aqueous System (Case 1)

Into a test tube (16×150 mm) were placed a phthalocyanine green suspension (5 mL: phthalocyanine green 16 mg/distilled water 200 mL) and the filtrate (evaporated to dryness) obtained in culture example 1 in a predetermined amount, followed by stirring for 15 seconds with a point mixer. After the stirring, the resulting mixture liquid was allowed to stand for three hours, and then the diameter of phthalocyanine green deposited on the bottom of the test tube was measured to evaluate the dispersibility from the diameter measured. That is, a greater diameter measured is indicative of better dispersibility. For comparison, the same procedure was taken with commercially available naphthalenesulfonate or lignin sulfonate. The results of measurement are shown in Table 18.

TABLE 18

| | Diameter (mm) | | | | | |
| --- | --- | --- | --- | --- | --- | --- |
| Test sample | 0 | 0.17 mg | 0.85 mg | 1.7 mg | 8.5 mg | 17 mg |
| Filtrate | 4 | 7 | 11 | 12 | 14 | 14 |
| Naphthalenesulfonate | 4 | 4 | 5 | 6 | 6 | 6 |
| Lignin sulfonate | 4 | 5 | 5 | 5 | 4 | 4 |

As seen from Table 18, the diameter measured in the case with use of the filtrate (evaporated to dryness) obtained in culture example 1 was much greater than that in the case without use of the filtrate and, hence, the former ease exhibited good dispersibility. Further, as to the degree of dispersibility, the case with use of the filtrate was superior to the cases respectively using naphthalenesulfonate and lignin satlfonate.

EXAMPLE 13

Evaluation of Dispersing Activity with Respect to an Organic Pigment in an Aqueous System (Case 2)

A homogenous copper phthalocyanine blue suspension was prepared by applying ultrasonic wave (for 10 minutes at the maximum output) to copper phthalocyanine blue (400 mg/water 400 mL) with an ultrasonic cleaner ("UT0205" manufactured by SHARP). 4.5 mL of this suspension was collected under stirring with a stirrer and each sample liquid (0.5 mL) was added to give a respective amount shown in Table 19. After having been stirred for 10 seconds with a point mixer, each suspension was allowed to stand on a vibration-free plate and measured for transmissivity of 660 nm light with lapse of time. The results of measurement are shown also in Table 19. It should be noted that the transmissivity of light serves as an indication of dispersibility, and a lower transmissivity is indicative of higher dispersibility.

TABLE 19

| | | Transmissivity (%) | | |
| --- | --- | --- | --- | --- |
| Test sample | Concentration (mg/mL) | 3 hrs later | 6 hrs later | 24 hrs later |
| No addition | — | 31 | 55 | 82 |
| t-butyl ester tetrasodium salt of S1 compound (preparation example 14) | 0.025 | 0 | 1 | 7 |
| | 0.05 | 0 | 0 | 4 |
| | 0.1 | 0 | 0 | 1 |
| Benzylamide tetrasodium salt of S1 compound (preparation example 15) | 0.025 | 0 | 1 | 8 |
| | 0.05 | 0 | 0 | 5 |
| | 0.1 | 0 | 0 | 3 |
| n-butylamide tetrasodium salt of S1 compound (preparation example 13) | 0.025 | 0 | 2 | 10 |
| | 0.05 | 0 | 1 | 8 |
| | 0.1 | 0 | 2 | 7 |
| sodium dodecylbenzenesulfonate | 0.025 | 20 | 23 | 36 |
| | 0.05 | 14 | 17 | 25 |
| | 0.1 | 4 | 6 | 9 |

As seen from Table 19, the case with use of a derivative of S1 compound as a test sample exhibited a marked improvement in transmissivity as compared with the case without use of such a derivative. As to the degree of dispersibility, the former case was superior to the case using sodium dodecylbenzensulfonate, and the difference in dispersibility between the two became more conspicuous when the added amount was low.

EXAMPLE 14

Evaluation of Dispersing Activity with Respect to an Organic Pigment in a Non-aqueous System (Case 1)

Into a test tube (16×150 mm) was scaled and collected 0.5 mL of a suspension of copper phthalocyanine blue in ethyl acetate (40 mg/10 mL) under stirring with a point mixer, and ethyl acetate (4.5 mL) was further added thereto.

To this suspension was added a solution of each of S1 and S2 anhydrides obtained in preparation example 1 in ethyl acetate (20 mg/2 mL), and ethyl acetate was further added thereto to give a total amount of 6 mL. This liquid was stirred with a point mixer for 15 seconds, treated with ultrasonic wave for 30 minutes, and then allowed to stand for 10 to 30 minutes. The resulting supernatant liquid (0.5 mL) was colle cted, admixed with ethyl acetate to give a total amount of 3 mL and then measured for absorbance at 660 wavelength. From the absorbance thus measured, the dispersibility was evaluated. The results are shown in Table 20.

TABLE 20

| Amount added | Absorbance (660 nm) | |
|---|---|---|
| (mg) | S1 anhydride | S2 anhydride |
| 0 | 0.62 | 0.38 |
| 2.5 | 0.66 | 0.47 |
| 5 | 1.27 | 0.99 |
| 10 | 1.86 | 1.51 |

As seen from Table 20, the case with use of the solution of S1 and S2 anhydrides in ethyl acetate exhibited a remarkable improvement in dispersibility as compared with the case without use of these compounds.

EXAMPLE 15

Evaluation of Dispersing Activity with Respect to an Organic Pigment in a Non-aqueous System (Case 2)

S0 anhydride obtained in preparation example 11 was treated in the same manner as in example 14. The resulting supernatant liquid (0.25 mL) was collected, admixed with ethyl acetate to give a total amount of 3 mL, and then measured for absorbance. From the absorbance thus measured, the dispersing activity was evaluated. The results are shown in Table 21.

TABLE 21

| Amount added (mg) | Absorbance (660 nm) |
|---|---|
| 0 | 0.14 |
| 0.5 | 0.84 |
| 1.0 | 0.89 |

As seen from Table 21, the case with use of the solution of S0 anhydride in ethyl acetate exhibited a remarkable improvement in dispersibility as compared with the case without use of the compound.

EXAMPLE 16

Evaluation of Dispersing Activity with Respect to an Organic Pigment in a Non-aqueous System (Case 3)

The same procedure as in example 14 except for the use of ethanol instead of ethyl acetate was performed. The amount of a supernatant liquid was 0.25 mL. From the absorbance thus measured, the dispersing activity was evaluated. The results are shown in Table 22.

TABLE 22

| Amount added | Absorbance (660 nm) | |
|---|---|---|
| (mg) | S1 anhydride | S2 anhydride |
| 0 | 0.01 | |
| 0.25 | 0.05 | 0.09 |
| 0.50 | 0.69 | 0.87 |
| 1.00 | 0.63 | 0.80 |

As seen from Table 22, the cases with use of the solution of S1 and S2 anhydrides in ethanol exhibited a remarkable improvement in dispersibility as compared with the case without use of the compounds.

EXAMPLE 17

Sequestering Ability Against Calcium Ion Under Alkaline Condition (pH13)

First, a liquid for measurement was prepared in the following manner. Potassium oxalate (0.6 g) was dissolved in 0.1N sodium hydroxide (500 mL), and in the resulting solution (10 mL) was dissolved pentasodium salt of S1 compound (40) mg) or heptasodium salt of S2 compound (40 mg) to give the liquid for measurement. As a titrant was used 2.2% calcium acetate solution.

The titrant was added dropwise to this liquid for measurement under stirring until the liquid for measurement became turbid by precipitation of calcium oxalate to determine the titer used A (mL). Another liquid for measurement not containing any one of the test samples was also measured in the same manner as above to determine the titer of blank B (mL). Based on the titers A and B, the sequestering ability against calcium ion was calculated according to the following formula. For comparison, an existing chelating agent (EDTA·4Na) was treated in the same manner as above to calculate its sequestering ability against calcium ion.

Sequestering ability against calcium ion [Ca ion (mg)/test sample (1 g)]=(A−B)×(1 g/test sample amount precisely weighed)×5 wherein the numeral "5" is the amount of Ca ion (5 mg) equivalent to 1 mL of the 2.2% calcium acetate solution.

The results obtained are shown in Table 23.

TABLE 23

| Test sample | Ca ion (mg/1 g of a test sample) |
|---|---|
| EDTA · 4Na | 92 |
| Pentasodium salt of S1 compound | 39 |
| Heptasodium salt of S2 compound | 59 |

The sequestering ability against calcium ion is one of the indications of a chelating action, and a greater value is indicative of higher chelating ability.

As seen from Table 23, heptasodium salt of S2 compound exhibited a chelating action which was more potent than pentasodium salt of S1 compound and substantially as potent as the existing chelating agent (EDTA·4Na).

EXAMPLE 18

Measurement of Surface Tension

According to the plate-hanging method of Wihelmy, pentasodium salt of S1 compound and heptasodium salt of S2 compound were measured for their surface tension. Specifically, a cleaned glass plate was hung vertically and the level of a sample liquid was raised to a predetermined position to dip the glass plate, and then the liquid level was lowered gently. At the time when the entire leading edge of the glass plate became flush with the liquid level, the load was measured by means of an electronic balance. The surface tension γ (dyn/cm) is found by the formula:

$$\gamma=(P+B-W)/[2(L+d)]$$

wherein P (g) represents the load at that time, L (cm) the width of the glass plate, d (cm) the thickness, B the buoyancy, and W the gravity.

In this test, the surface tension was found from $\gamma = P \times 203.3$. The measurement was conducted at room temperature (25° C.). The pentasodium salt of S1 compound and heptasodium salt of S2 compound were both measured for their surface tension within a range of $1 \times 10^{-5}$ to $1 \times 10^{-2}$ M. The results of determination are shown in Table 24.

TABLE 24

| Concentration (M) | Surface tension (dyn/cm) | |
|---|---|---|
| | Pentasodium salt of S1 compound | Heptasodium salt of S2 compound |
| $1 \times 10^{-5}$ | 71.4 | 70.7 |
| $5 \times 10^{-4}$ | 70.7 | 63.4 |
| $1 \times 10^{-4}$ | 68.9 | 60.8 |
| $5 \times 10^{-3}$ | 65.3 | 53.9 |
| $1 \times 10^{-3}$ | 62.4 | 51.4 |
| $5 \times 10^{-2}$ | 56.9 | 49.0 |
| $1 \times 10^{-2}$ | 51.4 | 46.9 |

As seen from Table 24, pentasodium salt of S1 compound and heptasodium salt of S2 compound exhibited a decrease in surface tension with increasing concentration, which was a characteristic of a surface active agent, and hence were each confirmed to have a surface activity.

EXAMPLE 19

Evaluation as a Detergent for Clothes (Detergent Activity Against Artificially Soiled Cloth)

A detergency test was conducted using a Launder-o-meter as a detergency tester by washing 15 pieces of artificially wet-soiled cloth (size: 5×5 cm, dirt composition: oleic acid 28.3%, triolein 15.6%, cholesterol oleate 12.2%, liquid paraffin 2.5%, squalene 2.5%, cholesterol 1.6%, gelatin 7.0%, soil matter 29.8% and carbon black 0.2–0.3%) available from SENTAKU KAGAKU KYOKAI (foundation) in a washing liquid (liquid temperature: 20° C.) of the composition shown in Table 25 for 10 minutes, followed by rinsing for three minutes.

Judgment was done in the following manner. The reflectivity of each of the 15 pieces of artificially soiled cloth was measured before and after the test by means of a spectrocolorizeter, and from the mean value of the measured values the detergency was calculated according to the formula of Kubelka and Munk. The ratio of the detergency calculated of a sample to the detergency of a washing liquid with no addition was found as a detergency ratio. The results of measurement are shown also in Table 25.

TABLE 25

| Basic washing liquid composition | Additive | Amount of additive | Detergency ratio |
|---|---|---|---|
| Sodium laurylbenzenesulfonate 0.20 g/L | Heptasodium salt of S2 compound | 0.25 g/L | 1.72 |
| Sodium salt of beef tallow fatty acid 0.03 g/L | Sodium tripolyphosphate | 0.25 g/L | 1.38 |
| Polyoxyethylene alkyl ether 0.02 g/L | Zeolite | 0.25 g/L | 1.72 |
| Sodium carbonate 0.10 g/L | Trisodium citrate | 0.25 g/L | 1.38 |
| Sodium silicate 0.10 g/L | No addition | — | 1.00 |

As seen from Table 25, the case with use of heptasodium salt of S2 compound exhibited a higher detergency than the case without use of the compound.

INDUSTRIAL APPLICABILITY

Since the compounds of the present invention are thus constituted, they can provide compounds originating from natural products which are capable of exhibiting excellent dispersing ability irrespective of the sort of dispersoid.

Further, the compounds of the present invention have been confirmed to have an action of masking interfering metal ions by chelating with the same and a surface activity, as well as the above-stated excellent dispersing action.

What is claimed is:

1. A polyenepolycarboxylic acid having the formula (1):

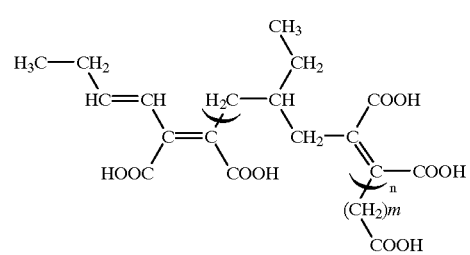

wherein n is an integer of 0 to 5, and m is an integer of 1 or 2, provided that m is 1 when n is 0, or a derivative thereof at the carboxyl group(s) or a salt thereof.

2. The polyenepolycarboxylic acid of claim 1, wherein m=1 and n=0 in the formula (1), or a derivative thereof at the carboxyl group(s) or a salt thereof.

3. The polyenepolycarboxylic acid of claim 1, wherein m=2 and n=1 in the formula (1), or a derivative thereof at the carboxyl group(s) or a salt thereof.

4. The polyenepolycarboxylic acid of claim 1, wherein m=2 and n=2 in the formula (1), or a derivative thereof at the carboxyl group(s) or a salt thereof.

5. The polyenepolycarboxylic acid of claim 1, wherein the derivative thereof at the carboxyl group is an acid anhydride.

6. The polyenepolycarboxylic acid of claim 1, which is a derivative thereof at the carboxyl group, wherein a portion of the carboxyl groups is ester, and the remainder thereof is acid anhydride groups.

7. The polyenepolycarboxylic acid of claim 1, wherein a portion of the carboxyl groups are derivative groups thereof, and the remainder of the carboxyl groups are in a form of a salt.

8. The polyenepolycarboxylic acid of claim 1, which is a salt, said salt being a salt of alkali metals, alkaline earth metals, ammonium, organic bases or amino acids.

9. The polyenepolycarboxylic acid of claim 1, which is a derivative thereof at the carboxyl group, and is an ester.

10. The polyenepolycarboxylic acid of claim 9, wherein said ester is a lower alkyl ester.

11. The polyenepolycarboxylic acid of claim 1, which is a derivative thereof at the carboxyl group, and is an amide.

12. The polyenepolycarboxylic acid of claim 11, wherein said amide is a maleimide.

13. The polyenepolycarboxylic acid of claim 11, wherein said amide is a lower alkyl amide.

14. The polyenepolycarboxylic acid of claim 11, wherein said amide is an arylamide.

15. A method for preparing a polyenepolycarboxylic acid represented by the formula (1) of claim 1, or acid anhydrides thereof or salts thereof, comprising the steps of:

a) cultivating a microorganism belonging to genus Talaromyces in a culture medium; and b) isolating from a resulting culture solution therefrom the polyenepolycarboxylic acids, or acid anhydrides thereof or salts thereof of claim 1.

16. The method of claim 15, wherein said microorganisms is Talaromyces sp. No. 10092 (FERM BP-6250).

17. A dispersant composition, comprising:

a) one or more polyenepolycarboxylic acid(s) having the formula (1) of claim 1, or derivatives thereof or salts thereof; and b) a carrier.

18. The dispersant composition of claim 17, containing the polyenepolycarboxylic acid(s) of the formula (1) wherein m=2 and n=0, or derivatives thereof at its carboxyl group(s) or their salts.

19. The dispersant composition of claim 17, containing the polyenepolycarboxylic acid(s) of the formula (1) wherein m=2 and n=1, or derivatives thereof at its carboxyl group(s) or their salts.

20. The dispersant composition of claim 17, containing the polyenepolycarboxylic acid(s) of the formula (1) wherein m=2 and n=2, or derivatives thereof at its carboxyl group(s) or their salts.

21. A dispersion, comprising:

a) an effective amount of one or more of the polyenepolycarboxylic acids having the formula (1) of claim 1; and b) a dispersoid.

22. The dispersion of claim 21, which is aqueous.

23. The dispersion of claim 21, which is non-aqueous.

24. The dispersion of claim 21, wherein the dispersoid comprises pigments, inks, fibers, paper, cosmetic substances, foods, paints, cement, concrete, rubber, plasters, pharmaceutical chemicals, agricultural chemicals, dyes, glazes, photographic film substances, magnetic materials, heavy oil or cleaning substances.

25. The dispersion of claim 21, wherein said one or more polyenepolycarboxylic acids are present in an amount of from 0.01 to 20 wt % based on the dispersoid.

\* \* \* \* \*